(12) United States Patent
Deutsch et al.

(10) Patent No.: US 7,403,647 B2
(45) Date of Patent: Jul. 22, 2008

(54) METHOD FOR IDENTIFYING AN IMAGE OF A WELL IN AN IMAGE OF A WELL-BEARING COMPONENT

(75) Inventors: Mordechai Deutsch, Doar Na Lev-HaSharon (IL); Menachem Kaufman, Petach Tikva (IL)

(73) Assignee: Seng Enterprises Ltd., Larnaca (CY)

( * ) Notice: Subject to any disclaimer, the term of this patent is extended or adjusted under 35 U.S.C. 154(b) by 556 days.

(21) Appl. No.: 10/938,951

(22) Filed: Sep. 13, 2004

(65) Prior Publication Data

US 2006/0057557 A1    Mar. 16, 2006

(51) Int. Cl.
*G06K 9/00* (2006.01)
(52) U.S. Cl. .................. 382/133; 128/922; 377/10; 435/40.51; 702/19
(58) Field of Classification Search .................. 382/100, 382/128, 133, 134; 128/922; 429/9, 96, 429/99; 377/10; 435/40.51; 702/19–21
See application file for complete search history.

(56) References Cited

U.S. PATENT DOCUMENTS

| 655,365 | A |   | 7/1900 | Johnson |
| 4,207,554 | A | * | 6/1980 | Resnick et al. ............... 382/133 |
| 4,308,351 | A |   | 12/1981 | Leighton et al. |
| 4,729,949 | A |   | 3/1988 | Weinreb et al. |
| 4,894,343 | A |   | 1/1990 | Tanaka et al. |
| 5,059,266 | A |   | 10/1991 | Yamane et al. |
| 5,204,055 | A |   | 4/1993 | Sachs et al. |
| 5,272,081 | A | * | 12/1993 | Weinreb et al. ............... 435/29 |
| 5,395,588 | A |   | 3/1995 | North, Jr. et al. |
| 5,428,451 | A |   | 6/1995 | Lea et al. |
| 5,506,141 | A |   | 4/1996 | Weinreb et al. |
| 5,627,045 | A |   | 5/1997 | Bochner et al. |
| 5,650,323 | A |   | 7/1997 | Root et al. |
| 5,707,869 | A |   | 1/1998 | Wolf et al. |
| 5,854,684 | A |   | 12/1998 | Stabile et al. |
| 5,905,031 | A |   | 5/1999 | Kuylen et al. |
| 6,046,426 | A |   | 4/2000 | Jeantette et al. |
| 6,066,285 | A |   | 5/2000 | Kumar |

(Continued)

FOREIGN PATENT DOCUMENTS

WO    WO 98/15356    4/1998

(Continued)

OTHER PUBLICATIONS

Aplin et al. "Protein-Derivatised Glass Coverslips for the Study of Cell-to-Substratum Adhesion", Analytical Biochemistry, 113: 144-148, 1981.

(Continued)

*Primary Examiner*—Bhavesh M. Mehta
*Assistant Examiner*—Anand Bhatnagar

(57) ABSTRACT

A method for identifying images of wells in an image of a well-bearing object such as multiwell plates or picowell carriers is provided. An observation component, such as a camera, is used to approach focus of a focal point of a well-bottom. An image of the focal point is acquired. The image of the well-bottom focal point is then used as a reference point or used to define a reference point from which to identify the image of the well in the image of the well-bearing component and from which to delineate the borders of the well.

33 Claims, 25 Drawing Sheets
(11 of 25 Drawing Sheet(s) Filed in Color)

U.S. PATENT DOCUMENTS

| | | |
|---|---|---|
| 6,103,479 A | 8/2000 | Taylor |
| 6,117,612 A | 9/2000 | Halloran et al. |
| 6,206,672 B1 | 3/2001 | Grenda |
| 6,228,437 B1 | 5/2001 | Schmidt |
| 6,238,614 B1 | 5/2001 | Yang et al. |
| 6,329,195 B1 | 12/2001 | Pfaller |
| 6,333,192 B1 | 12/2001 | Petitte et al. |
| 6,338,964 B1 | 1/2002 | Matanguihan et al. |
| 6,342,384 B1 | 1/2002 | Chung et al. |
| 6,344,354 B1 | 2/2002 | Webster et al. |
| 6,345,115 B1* | 2/2002 | Ramm et al. ............... 382/133 |
| 6,372,494 B1 | 4/2002 | Naughton et al. |
| 6,376,148 B1 | 4/2002 | Liu et al. |
| 6,377,721 B1 | 4/2002 | Walt et al. |
| 6,378,527 B1 | 4/2002 | Hungerford et al. |
| 6,383,810 B2 | 5/2002 | Fike et al. |
| 6,403,369 B1 | 6/2002 | Wood |
| 6,410,309 B1 | 6/2002 | Barbera-Guillem et al. |
| 6,413,744 B1 | 7/2002 | Morris et al. |
| 6,413,746 B1 | 7/2002 | Field |
| 6,455,310 B1 | 9/2002 | Barbera-Guillem et al. |
| 6,465,000 B1 | 10/2002 | Kim |
| 6,465,205 B2 | 10/2002 | Hicks, Jr. |
| 6,468,788 B1 | 10/2002 | Marotzki |
| 6,479,252 B1 | 11/2002 | Barbera-Guillem et al. |
| 6,489,144 B1 | 12/2002 | Lau |
| 6,492,148 B1 | 12/2002 | van Loon et al. |
| 6,492,163 B1 | 12/2002 | Yoo et al. |
| 6,495,340 B2 | 12/2002 | Huberman et al. |
| 6,506,598 B1 | 1/2003 | Andersen et al. |
| 6,511,430 B1 | 1/2003 | Sherar et al. |
| 6,528,286 B1 | 3/2003 | Ryll |
| 6,544,788 B2 | 4/2003 | Singh |
| 6,555,365 B2 | 4/2003 | Barbera-Guillem et al. |
| 6,569,422 B1 | 5/2003 | van Loon et al. |
| 6,588,586 B2 | 7/2003 | Abasolo et al. |
| 6,589,765 B1 | 7/2003 | Choi et al. |
| 6,593,101 B2* | 7/2003 | Richards-Kortum et al. .. 435/29 |
| 6,593,140 B1 | 7/2003 | Field |
| 6,610,516 B1 | 8/2003 | Andersen et al. |
| 6,627,426 B2 | 9/2003 | Biddle et al. |
| 6,632,619 B1 | 10/2003 | Harrison et al. |
| 6,635,448 B2 | 10/2003 | Bucciarelli et al. |
| 6,642,050 B1 | 11/2003 | Goto et al. |
| 6,645,757 B1 | 11/2003 | Okandan et al. |
| 6,649,408 B2 | 11/2003 | Bailey et al. |
| 6,660,501 B2 | 12/2003 | Field |
| 6,667,034 B2 | 12/2003 | Palsson et al. |
| 6,670,180 B2 | 12/2003 | Block |
| 6,670,184 B2 | 12/2003 | Chiarello et al. |
| 6,673,591 B2 | 1/2004 | Lau |
| 6,686,190 B2 | 2/2004 | Lau |
| 6,689,594 B1 | 2/2004 | Hänni et al. |
| 6,692,961 B1 | 2/2004 | Judd et al. |
| 7,139,415 B2* | 11/2006 | Finkbeiner ............... 382/128 |
| 2002/0106715 A1 | 8/2002 | Huberman et al. |
| 2002/0150909 A1* | 10/2002 | Stuelpnagel et al. ........... 435/6 |
| 2002/0173033 A1 | 11/2002 | Hammerick et al. |
| 2002/0189374 A1 | 12/2002 | DeSilets et al. |
| 2003/0030184 A1 | 2/2003 | Kim et al. |
| 2003/0032204 A1 | 2/2003 | Walt et al. |
| 2003/0082818 A1* | 5/2003 | Bahnson et al. ............... 436/63 |
| 2003/0104494 A1 | 6/2003 | Ravkin et al. |
| 2003/0124716 A1 | 7/2003 | Hess et al. |
| 2003/0189850 A1 | 10/2003 | Sasaki et al. |
| 2003/0211458 A1 | 11/2003 | Sunray et al. |
| 2004/0235143 A1 | 11/2004 | Sasaki et al. |
| 2005/0014201 A1* | 1/2005 | Deuthsch .................... 435/7.2 |
| 2005/0064524 A1 | 3/2005 | Deutsch et al. |
| 2006/0041384 A1* | 2/2006 | Kermani et al. ............... 702/19 |
| 2007/0178607 A1* | 8/2007 | Prober et al. ................ 436/522 |

FOREIGN PATENT DOCUMENTS

| | | |
|---|---|---|
| WO | WO 98/35223 | 8/1998 |
| WO | WO 99/45357 | 9/1999 |
| WO | WO 99/47922 | 9/1999 |
| WO | WO 01/35071 | 5/2001 |
| WO | WO 01/88176 | 11/2001 |
| WO | WO 02/26114 | 4/2002 |
| WO | WO 02/063034 | 8/2002 |
| WO | WO 03/035824 | 1/2003 |
| WO | WO 03/011451 | 2/2003 |
| WO | WO 03/056330 | 7/2003 |
| WO | WO 2004/077009 | 9/2004 |
| WO | WO 2004/113492 | 12/2004 |
| WO | WO 2005/007796 | 1/2005 |

OTHER PUBLICATIONS

Mrksich et al. "Using Self-Assembled Monolayers to Understand the Interactions of Man-Made Surfaces with Proteins and Cells", Annual Rev. Biomol. Struct., 25: 55-78, 1996.

Singhvi et al. "Engineering Cell Shape and Function", Science, 264: 696-698, 1994.

Dolbeare "Fluorescent Staining of Enzymes for Flow Cytometry", Methods Cell Biol., 33(Chap.8): 81-88, 1990.

Klingel et al. "Flow Cytometric Determination of Serine Proteinase Activities in Living Cells With Rhodamine 110 Substrates", Methods Cell Biol., 41(Chap.29): 449-460, 1994.

Malin-Berdel et al. "Flow Cytometric Determination of Esterase and Phosphatase Activities and Kinetics in Hematopoietic Cells With Fluorogenic Substrates", Cytometry, 1(3): 222-228, 1980.

Nooter et al. "On-Line Flow Cytometry. A Versatile Method for Kinetic Measurement", Methods Cell Biol., 41(Chap.32): 509-526, 1994.

Turek et al. "Leucine Aminopeptidase Activity by Flow Cytometry", Methods Cell Biol., 41(Chap.30): 461-468, 1994.

Watson et al. "Enzyme Kinetics", Methods Cell Biol., 41: 469-508, 1994.

Bedner et al. "Enzyme Kinetic Reactions and Fluorochrome Uptake Rates Measured in Individual Cells by Laser Scanning Cytometry", Cytometry, 33(1): 1-9, 1998. Abstract, p. 2, col. 1, §4-col. 2, §1, p. 8, col. 2, §2.

Sunray et al. "Cell Activation Influences Cell Staining Kinetics", Spectrochimica Part A, 53: 1645-1653, 1997.

Eisenthal et al. "Infection of K562 Cells With Influenza A Virus Increases Their Susceptibility to Natural Killer Lysis", Pathobiology, 65: 331-340, 1997.

Deutsch et al. "Apparatus for High-Precision Repetitive Sequential Optical Measurement of Living Cells", Cytometry, 16: 214-226, 1994.

Sunray et al. "Determination of the Michaelis-Menten Constant (Km) of Intracellular Enzymatic Reaction for Individual Live Lymphocytes", Cytometry Supplement, 10: 68-69, & The XX Congress of the International Society for Analytical Cytology, Montpellier, F, 2000.

Darzynkiewicz et al. "Laser-Scanning Cytometry: A New Instrumentation With Many Applications", Experimental Cell Research, 249(1): 1-12, 1999. Abstract, p. 2, col. 2, §4-p. 4, col. 2, §2, p. 8, col. 1, §1-col. 2, §2.

Sunray et al. "The Trace and Subgrouping of Lymphocyte Activation by Dynamic Fluorescence Intensity and Polarization Measurements", Biochemical and Biophysical Research Communications, 261(3): 712-719, 1999. Abstract, p. 713, col. 1, §5, col. 2, §7-p. 714, col. 1, §1.

Sunray et al. "Determination of Individual Cell Michaelis-Menten Constants", Cytometry, 47(1): 8-16, 2002.

Dive et al. "Improved Methodology for Intracellular Enzyme Reaction and Inhibition Kinetics by Flow Cytometry", Cytometry Journal of Society for Analytical Cytology, 8(6): 552-561, 1987.

Koh et al. "Poly(Ethylene Glycol) Hydrogel Microstructures Encapsulating Living Cells", Langmuir, 18(7): 2459-2462, 2002. p. 2459-2462, Fig.3.

Lansing Taylor et al. "Real-Time Molecular and Cellular Analysis: The New Frontier of Drug Discovery", Current Opinion in Biotechnology, 12: 75-81, 2001.

Burlage et al. "Living Biosensors for the Management and Manipulation of Microbial Consortia",Annual. Rev. Microbiol., 48: 291-309, 1994.

Riedel et al. "Arxula Adeninivorans Based Sensor for the Estimation of Bod", Analytical Letters, 31(1): 1-12, 1998.

Simonian et al. "Microbial Biosensors Based on Potentiometric Detection", Methods in Biotechnology,6, chapter 17: 237-248, 1998.

Arikawa et al. "Microbial Biosensors Based on Respiratory Inhibition", Methos in Biotechnology,6, chapter 16: 225-235, 1998.

* cited by examiner

METHOD FOR IDENTIFYING AN IMAGE OF A WELL IN AN IMAGE OF A WELL-BEARING COMPONENT

FIELD AND BACKGROUND OF THE INVENTION

The present invention relates to the field of cellular biology and more particularly, to an improved device and method for the study of cells. Specifically, the present invention is a method and a device for identification of the image of individual wells in an image of a well-bearing component so as to allow efficient image analysis and signal detection of cells held in the wells.

Combinatorial methods in chemistry, cellular biology and biochemistry are essential for the near simultaneous preparation of multitudes of active entities such as molecules. Once such a multitude of molecules is prepared, it is necessary to study the effect of each one of the active entities on a living organism.

The study of the effects of stimuli such as exposure to active entities on living organisms is preferably initially performed on living cells. Since cell-functions include many interrelated pathways, cycles and chemical reactions, the study of an aggregate of cells, whether a homogenous or a heterogeneous aggregate, does not provide sufficiently detailed or interpretable results: rather a comprehensive study of the biological activity of an active entity may be advantageously performed by examining the effect of the active entity on a single isolated living cells. Thus, the use of single-cell assays is one of the most important tools for understanding biological systems and the influence thereupon of various stimuli such as exposure to active entities.

The combinatorial preparation of a multitudes of active entities coupled with the necessity of studying the effect of each one of the active entities on living organisms using a single-cell assay, requires the development of high-throughput single live cell assays. There is a need for the study of real-time responses to treatment in large and heterogeneous cell populations at an individual cell level. In such studies it is essential to have the ability to define multiple characteristics of each individual cell, as well as the individual cell response to the experimental intervention of interest.

In the art, various different methods for studying living cells are known.

Multiwell plates having 6, 12, 48, 96, 384 or even 1536 wells on a standard ca. 8.5 cm by ca. 12.5 cm footprint are well known in the art. Such multiwell plates are provided with an 2n by 3n array of rectangular packed wells, n being an integer. The diameter of the wells of a plate depends on the number of wells and is generally greater than about 250 microns (for a 1536 well plate). The volume of the wells depends on the number of wells and the depth thereof but generally is greater than $5 \times 10^{-6}$ liter (for a 1536 well plate). The standardization of the formats of multiwell plates is a great advantage for researchers as the standardization allows the production of standardized products including robotic handling devices, automated sample handlers, sample dispensers, plate readers, observation components, plate washers, software and such accessories as multifilters.

Multiwell plates are commercially available from many different suppliers. Multiwell plates made from many different materials are available, including but not limited to glass, plastics, quartz and silicon. Multiwell plates having wells where the inside surface is coated with various materials, such as active entities, are known.

Although exceptionally useful for the study of large groups of cells, multiwell plates are not suitable for the study of individual cells or even small groups of cells due to the large, relative to the cellular scale, size of the wells. Cells held in such wells either float about a solution or adhere to a well surface. When cells float about in a well, specific individual cells are not easily found for observation. When cells adhere to a well surface, the cells adhere to any location in the well, including anywhere on the bottom of the well and on the walls of the well. Such variability in location makes high-throughput imaging (for example for morphological studies) challenging as acquiring an individual cell and focusing thereon is extremely difficult. Such variability in location also makes high-throughput signal processing (for example, detection of light emitted by a single cell through fluorescent processes) challenging as light must be gathered from the entire area of the well, decreasing the signal to noise ratio. Further, a cell held in a well of a multiwell plate well can be physically or chemically manipulated (for example, isolation or movement of a single selected cell or single type of cell, changing media or introducing active entities) only with difficulty. Further, the loading of multiwell plates as expressed in terms of cells held singly in the wells per unit area is very low (about 1536 cells in 65 cm$^2$, or 24 cells cm$^{-2}$) Thus, multiwell plates are in general only suitable for the study of homogenous or heterogenous aggregates of cells as a group.

An additional disadvantage of multiwell plates is during the study of cells undergoing apoptosis. One method of studying cells is by exposing cells in a monolayer of cells adhered to the bottom of the well of a multiwell plate to a stimulus. As is known to one skilled in the art, one of the most important processes that a cell potentially undergoes is apoptosis and it is highly desirable to observe a cell throughout the apoptosis process. However, once a cell begins the apoptosis process, the adhesion of the cell to the bottom of the well is no longer sufficient: the cell detaches from the bottom and is carried away by incidental fluid currents in the well. The cell is no longer observable and its identity lost.

An additional disadvantage of multiwell plates is in the study of non-adhering cells. Just as cells undergoing apoptosis, in multiwell plates non-adhering cells can be studied as individuals only with difficulty. Considering that non-adhering cells are crucial for research in drug discovery, stem cell therapy, cancer and immunological diseases detection, diagnosis, therapy this is a major disadvantage. For example, blood contains seven heterogeneous types of non-adherent cells, all which perform essential functions, from carrying oxygen to providing immunity against disease.

In the art, a number of method and devices have been developed for the study of individual cells or a small number of cells as a group. Many such methods are based on using picowell-bearing device. A picowell-bearing device is a device for the study of cells that has at least one picowell-bearing component for study of cells. A picowell-bearing component is a component having at least one, but generally a plurality of picowells, each picowell configured to hold at least one cell. The term "picowell" is general and includes such features as dimples, depressions, tubes and enclosures. Since cells range in size from about 1 microns to about 100 (or even more) microns diameter there is no single picowell size that is appropriate for holding a single cell of any type. That said, the dimensions of the typical individual picowell in the picowell-bearing components known in the art have dimensions of between about 1 microns up to about 200 microns, depending on the exact implementation. For example, a device designed for the study of single isolated 20 micron cells typically has picowells of dimensions of about 20 microns. In other cases, larger picowells are used to study the interactions of a few cells held together in one picowell. For example, a 200 micron picowell is recognized as being useful for the study of the interactions of two or three cells, see PCT patent application IL01/00992 published as WO 03/035824.

One feature that increases the utility of a picowell-bearing device is that each individual picowell is individually addressable. By individual addressability is meant that each picowell can be registered, found or studied without continuous observation. For example, while cells are held in picowells of a picowell-bearing component, each cell is characterized and the respective picowell where that cell is held is noted. When desired, the observation component of the picowell-bearing device is directed to the location of the picowell where a specific cell is held. One method of implementing individual addressability is by the use of fiducial points or other features (such as signs or labels), generally on the picowell-bearing component. Another method of implementing individual addressability is by arranging the picowells in a picowell-array and finding a specific desired picowell by counting. Another method of implementing individual addressability is by providing a dedicated observation component for each picowell.

In the art, the picowell-bearing component of a picowell-bearing device is often a chip, a plate or other substantially planar component. Herein such a component is termed a "carrier". In the art, there also exist non-carrier picowell-bearing components of picowell-bearing devices, for example, bundles of fibers or bundles of tubes.

Mrksich and Whitesides, *Ann. Rev. Biophys. Biomol. Struct.* 1996, 25, 55-78; Craighead et al., *J. Vac. Sci. Technol.* 1982, 20, 316; Singhvi et al., *Science* 1994, 264, 696-698; Aplin and Hughes, *Analyt. Biochem.* 1981, 113, 144-148 and U.S. Pat. No. 5,324,591 all teach of devices including arrays of spots of cell-attracting or cell-binding entities on a plate. In such devices, the spots serve as picowells, binding cells through a variety of chemical bonds. In such devices, the plate is the picowell-bearing component of the device. Due to the size of the spots, each such picowell generally holds more than one cell. To reduce interaction between cells held at different picowells, the spots must be spaced relatively far apart, reducing loading as expressed in terms of picowells per unit area. Even with generous spacing, in such picowell-bearing components held cells are not entirely isolated from mutual interaction, nor can cells be subject to individual manipulation. The fact that the cells are not free-floating but are bound to the plate through some interaction necessarily compromises the results of experiments performed.

In U.S. Pat. No. 6,103,479, the picowell-bearing component is a transparent carrier provided with a non-uniform array of picowells, each well functionalized with chemical entities that bind to cells specifically or non-specifically. Each picowell is of approximately 200 to 1000 micron diameter and is configured to hold a plurality of cells. The inter picowell areas are hydrophobic so as not to attract cells. In addition to the carrier, a device of U.S. Pat. No. 6,103,479 is provided with a glass, plastic or silicon chamber-bearing plate in which individually addressable microfluidic channels are etched, the chamber-bearing plate configured to mate with the carrier. When mated, the carrier and chamber-bearing plate constitute a cassette in which each cell is bound to the carrier and isolated in a chamber provided with an individual fluid delivery system. Reagents are provided through the fluid delivery system and observed by the detection of fluorescence. In order to provide space for the walls of the chambers, the inter picowell areas of the carrier are relatively large, reducing loading as expressed in terms of picowells per unit area. Subsequent to study, the cassette is separated into the two parts and the micro-patterned array of cells processed further. In some embodiments, the chamber-bearing plate is made of polytetrafluoroethylene, polydimethylsiloxane or an elastomer. As held cells do not make contact with the chamber-bearing plate it is not clear what advantages are to be had when providing a chamber-bearing plate of such esoteric materials.

In U.S. patent application Ser. No. 10/199,341, a device is taught for trapping a plurality of dielectric objects (such as cells), each individual object in an individual light beam produced by an optical array.

In U.S. Pat. No. 4,729,949, a device is taught for trapping individual cells in a picowell-bearing carrier, the carrier being substantially a plate having a plurality of picowells that are individually-addressable tapered apertures of a size to hold individual cells. Suction applied from the bottom surface of the plate where the picowells are narrow creates a force that draws cells suspended in a fluid above the carrier into the wide end of the picowells on the surface of the carrier to be held therein. Using the teachings of U.S. Pat. No. 4,729,949 a specific group of cells (having dimensions similar to that of the wide end of the picowells) can be selected from amongst a group of cells and held in the carrier. Although the cells are subjected to common stimuli, the fact that the picowells are individually addressable allows the effect of a stimulus on an individual cell to be observed. A carrier of U.S. Pat. No. 4,729,949, is generally made of metal such as nickel and prepared using standard photoresist and electroplating techniques. In a carrier of U.S. Pat. No. 4,729,949, the inter picowell areas of the carrier are relatively large, leading to a low loading as expressed in terms of picowells per unit area. Further, the suction required to hold cells in picowells of a carrier of U.S. Pat. No. 4,729,949 deforms held cells and makes a significant portion of the cell membranes unavailable for contact, both factors that potentially compromise experimental results. Study of cells with non-fluorescence based methods generally gives poor results due to reflections of light from the carrier.

In PCT patent application U.S.99/04473 published as WO 99/45357 is taught a picowell-bearing component produced by etching the ends of a bundle of optical fibers (apparently of glass) while leaving the cladding intact to form a picowell-bearing component that is a bundle of tubes. The size of the hexagonal picowells is demonstrated to be as small as 7 micron wide, 5 micron deep and having a volume of about $1.45 \times 10^{-13}$ liter. The inter picowell area is quite large due to the thickness of the cladding of the optical fibers. Light emitted by cells held in each picowell are independently observable through a respective optical fiber. In some embodiments, the inside surface of the picowells is coated with a film of materials such as collagen, fibronectin, polylysine, polyethylene glycol, polystyrene, fluorophores, chromophores, dyes or a metal. Loading the picowell-bearing component of PCT patent application U.S.99/04473 includes dipping the optical fiber bundle in a cell suspension so that cells adhere to the picowells. There are a number of disadvantages to the teachings of PCT patent application U.S.99/04473. The fact that the cells are studied only subsequent to adhesion to the picowells necessarily influences the results of experiments performed. Since cell proliferation generally begins soon after adhesion, it is not known if a detected signal is produced by a single cell or a plurality of cells. It is is not clear where exactly in a picowell a cell is held and therefore what percentage of light emitted from a cell travels to a detector. The fact that emitted light travels through an optical fiber leads to loss of time-dependent and phase information.

In unpublished copending PCT patent application IL04/00192 of the Applicant filed Feb. 26, 2004 is taught a picowell-bearing component produced by bundling together glass capillaries, each glass capillary attached to an independent fluid flow generator such as a pump. A cell held in a first picowell is transferred to a second picowell by the simultaneous application of an outwards flow from the first picowell and an inwards flow into the second picowell.

A preferred device for the study of cells is described in PCT patent application IL01/00992 published as WO 03/035824 of the Applicant. The device 10, depicted in FIG. 1, is provided with a transparent carrier 12 as a picowell-bearing component. Carrier 12 is substantially a sheet of transparent material (such as glass or polystyrene) on the surface of which features such as inlet connectors 14, fluid channels 16, picowells (in FIG. 1, a picowell-array 18), a fluid reservoir 20 and an outlet connector 22. Carrier 12 is immovably held in a holder 24 having a cutout window of a size and shape to accept carrier 12. Other components of device 10 not depicted include flow generators, observation components, external tubing and the like. When a cover slip (not depicted) is placed or integrally formed with carrier 12, fluid channels 16, picowell-array 18 and reservoir 20 are sealed forming channels that allow transport of fluids and reagents to cells held in picowell-array 18. The picowells are configured to hold a predetermined number of cells (one or more) of a certain size and are preferably individually addressable both for examination and manipulation.

FIG. 2 is a reproduction of a photograph of a different carrier 26 held in a holder 24. A first syringe 28 as an inlet flow generator is in communication with an inlet connector 14 by a capillary tube 30. Inlet connector 14 is in communication with picowell-array 18 through a fluid passage 16. Picowell-array 18 is in communication with outlet connector 22 through a fluid passage 16. A second syringe 32 as an outlet flow generator is in communication with outlet connector 22 through capillary tube 34.

PCT patent application IL01/00992 also teaches methods of physically manipulating cells held in a picowell-bearing device using, for example, individually addressable microelectrodes (found in the picowells or in the cover slip) or optical tweezers. Typical physical manipulations include moving selected cells into or out of specific picowells. One useful method that is implemented using a device of PCT patent application IL01/00992 is that cells, each held alone in a respective picowell, are examined (either in the presence or absence of reagents) and based on the results of the examination, cells with a certain characteristic are selected to remain in a respective picowell while cells without the certain characteristic are removed from a respective picowell and ejected by the application of a flow in parallel to the surface of the carrier, generated by a flow generator.

An additional feature of the teachings of PCT patent application IL01/00992 is that, in some embodiments, the picowells are juxtaposed, that is, the area occupied by a picowell-array is substantially entirely made up of picowells with little or no inter picowell area, see FIG. 3. FIG. 3 is a reproduction of a photograph of part of a picowell-array 18 from the top of a carrier 12 of PCT patent application IL01/00992. In FIG. 3 is seen a plurality of hexagonal picowells 36, some populated with living cells 38. It is seen that the inter picowell areas 40 make up only a minor percentage of the total area of picowell-array 18. This feature allows near tissue-density packing of cells, especially in single-cell picowell configurations. For example, a typical device of PCT patent application IL01/00992 having a 2 mm by 2 mm picowell-array of hexagonally-packed juxtaposed picowells of 10 micron diameter and no inter picowell area includes about 61600 picowells. This feature also allows simple picowell loading: a fluid containing suspended cells is introduced in the volume above the picowells. Since there is little inter picowell area, cells settle in the picowells.

One of the challenges of well-bearing devices known in the art for the study of single living cells, especially picowell-bearing devices, is of information acquisition.

One type of information acquisition is manual image analysis. Manual image analysis involves a cell biology expert visually inspecting cells, for example using an observation component equipped with optical magnification means such as a microscope and drawing conclusions based on the visual inspection. Manual image analysis is time-consuming, incompatible with high-throughput studies and is not generally applicable.

Two other type of information acquisition are automatic image analysis and automatic signal acquisition.

In automatic image analysis, high-resolution optical data is acquired substantially continuously for all wells of interest and cells held therein. A disadvantage of using automatic image analysis is that there is no easy way to sift through the massive amount of information acquired to identify important events from amongst all the images acquired.

In automatic signal analysis, one or limited number of signal channels, usually corresponding to a light intensity, are acquired as a function of time for each well and cells held therein substantially continuously. Often, the signal channels acquired correspond to different wavelengths of light emitted by fluoresence processes occuring in the wells.

One of the greatest challenges in both automatic image analysis and automatic signal analysis is the delineation of the borders of a single cell. For example, in FIG. 4 is depicted a reproduction of a transparent light image of MALT-4 cells on a glass plate. Individual cells and borders thereof were automatically determined. In many cases, cells are not identified. For example, in the upper left corner of FIG. 4, an aggregate of three cells designated "159" is identified to be one cell. In the middle right side of FIG. 4, the borders of cells designated as "439" and "438" are improperly delineated. In both such cases, analysis of an image or of a signal gives completely wrong results. Even when cells are held in picowells 36, for example, as depicted in FIG. 3, it is difficult to delineate the borders of wells and of cells held therein, especially when slight shifting of the picowell-bearing component relative to the field of view occurs, whether due to physical motion of the picowell-bearing component or as a result of motion of the observation component. Further, due to the fact that the material from which wells are made is not invisible, distortions, reflections, diffractions and the image of the picowell walls often make delineation of cells difficult. For example, differentiating cell 42 from cell 44 in FIG. 3 is a difficult task. It is important to note that even the imperfect methods known in the art are time consuming, expensive in terms of calculation resources, not robust and in general unsuited for high-throughput applications.

The problem of delineating the borders of a cell for automatic signal analysis is even greater. When automatic signal analysis is implemented, it is desired that the implementation be quick, robust and is directed for high-throughput analysis of many cells. In such applications, it is not practical to have a time consuming cell-identification or picowell-identification step. In addition, if the borders of the cell or picowells are not clearly delineated, the quality of the data is seriously compromised. For example, when a cell is delineated conservatively, and only a portion of a signal emitted by a cell is acquired the values of the acquired signal will be innaccurate, especially in cases where signals are not emitted from all areas of a cell homogenously. For example, when a cell is delineated too broadly and signals from neighboring cells are also acquired the signal to noise ratio decreases. An additional problem arises when what is to be detected is not light emitted by a cell itself but rather light emitted by chromatogenic or fluorogenic entitities in the medium in the immediate area of the cell, for example the medium held together with the cell in the same picowell. In such experiments it is critical to know the exact borders of the picowell in which a cells is held.

In the art, a number of solutions based on providing each well with a dedicated observation system have been proposed.

As discussed above in PCT patent application U.S.99/04473 is taught a picowell-bearing component produced by etching the ends of a bundle of optical fibers to form a picowell-bearing component where a cell held inside such a picowell necessarily is associated with an adressable optical fiber that tranports light emitted from the picowell to a detector for signal acquisition. As stated above, amongst other problems associated with the device of PCT patent application U.S.99/04473, the fact that the emitted light travels through an optical fiber leads to loss of time dependent and phase information. Further, the device of PCT patent application U.S.99/04473 is not suitable for acquiring high-resolution images.

A preferred method of automatic image acquisition where a well and the contents thereof are clearly delineated is described, for example, in PCT patent application IL01/000992 where in one embodiment is taught a device having an individual microlens dedicated to the continuous observation of every picowell of the picowell-bearing component and cells held therein. Such a method requires a highly expensive observation system, including a dedicated, accurately crafted and expensive microlens array. Further, such a microlens array must be located above the picowell array and is generally exposed to the medium in which cells are held.

It would be highly advantageous to have a device and methods for the study of cells not having at least some of the disadvantages of the prior art.

SUMMARY OF THE INVENTION

The present invention successfully addresses at least some of the shortcomings of the prior art by providing a method for identifying the image of a well in an image of a well-bearing component as well as of a device for implementing the method of the present invention. Embodiments of the present invention also provide for the quick, accurate and robust delineation of the borders of the images of the well., The present invention uses the optical properties of well-bottoms to identify the images of respective wells of a well-bearing component. Some or all embodiments of the present invention have advantages including applicability to occupied and unoccupied wells, delineation of images of signal-less occupied wells, allow the use of observation components such as CCD devices as multi-signal detectors, allows delineation of a well image irrespective of the well-bearing component orientation and allows the observation component to be located above or below the well-bearing component.

According to the teachings of the present invention there is provided a method of identifying an image of a well in an image of at least part of a well-bearing component comprising: illuminating the well-bearing component with a locating light source disposed on a first side of the well-bearing component; and acquiring an image of a focal point (real or imaginary) of a bottom of the well produced by light from the locating light source passing through the bottom of the well.

In an embodiment of the present invention, based on the image of the focal point, a reference point for identifying an area in an acquired image of the well-bearing component is determined, the area to be considered as being part of the image of the well. Preferably, based on the reference point, the area is delineated.

In an embodiment of the present invention, an image of the well-bearing component is acquired. Preferably while the well-bearing component is illuminated with an observation light source. According to a feature of the present invention, an observation component for acquiring the image of the well-bearing component is provided and the focus of the observation component is adjusted so as to acquire an image of the well-bearing component or of the contents of wells, such as cells held in wells.

In an embodiment of the present invention, based on the image of the focal point, a reference point for identifying an area in the acquired image of the well-bearing component is determined, the area defined as part of the image of the well.

According to a feature of the present invention, based on the reference point, borders of the area defined as part of the image of the well are delineated.

According to a feature of the present invention, an observation component for acquiring the image is provided, the observation component including an array of light-responsive elements; and designating the output of a group of light-responsive elements corresponding to the delineated area as corresponding to the image of the well.

In an embodiment of the present invention signals making up the area are summed so as to produce a limited number of signals characterizing the well.

In an embodiment of the present invention, the image of the well-bearing component acquired is pixelated and the summing of signals is substantially summing pixels making up the area. In an embodiment of the present invention, an observation component for acquiring the image is provided, the observation component including an array of light-responsive elements; and the summing up of the pixels is substantially summing up output signals from the light-responsive elements. According to a feature of the present invention, the signals have an intensity, the intensity being related to an intensity of light arriving from a part of the well. According to a feature of the present invention, the signals have an intensity, the intensity being related to an intensity of a component frequency of light arriving from a part of the well.

In an embodiment of the present invention, an observation component for acquiring the image of the focal point is provided, and the focus of the observation component is adjusted so as to acquire an image of the focal point. Preferably, adjusting the focus of the light-detection component is so that the image of the focal point of the bottom of the well is distinct from an image of a focal point produced by light passing through a bottom of a second well of the well-bearing component.

In an embodiment of the present invention, adjusting the focus of the light-detection component is so that the size of the image of the focal point of the bottom of the well is substantially a minimum.

In an embodiment of the present invention, the reference point is defined as being the image of the focal point.

In an embodiment of the present invention, the reference point is defined as being the center of the image of the focal point.

In an embodiment of the present invention, an area defined as part of the image of the well is delineated as a circle about the reference point.

According to the teachings of the present invention, there is provided a method for acquiring data comprising: a) providing a substantially planar well-bearing component having a lower surface, an upper surface, and a plurality of wells having refractive well-bottoms disposed on the upper surface and an observation component configured to observe a first of the two surfaces; b) projecting light through the well-bottoms from a second of the two surfaces; c) acquiring an image of a focal point (imaginary or real) of a well-bottom using the observation component; d) acquiring at least one image of the well-bearing component using the observation component; and e) using the image of the focal point of the well-bottom to determine a reference point for identifying an image of a respective well in the image of the well-bearing component.

Preferably, the well-bottoms have a $C_\infty$ rotation axis. Preferably, the $C_\infty$ rotation axis is substantially perpendicular to the focal plane of the observation component. Preferably, the light projected is substantially parallel to the rotation axis. Preferably, the light projected is collimated.

In an embodiment of the present invention, the first of the two surfaces is the lower surface and the second of the two surface is the upper surface. In an embodiment of the present invention, the first of the two surfaces is the upper surface and the second of the two surface is the lower surface.

In an embodiment of the present invention, prior to acquiring the image of the focal point, the focus of the observation component is adjusted. Preferably, the focus is adjusted to an extent where two images of two focal points produced by two well-bottoms are distinct. In an embodiment of the present invention, the focus is adjusted to an extent where the size of the image of the focal point is substantially minimal.

In an embodiment of the present invention, acquiring at least one image of the well-bearing component includes detecting light emitted by fluoresence.

In an embodiment of the present invention, acquiring at least one image of the well-bearing component includes detecting light reflected from the first of the two surfaces.

In an embodiment of the present invention, prior to acquiring at least one image of the well-bearing component, the focus of the observation component is adjusted to focus on contents of the wells.

In an embodiment of the present invention, prior to acquiring at least one image of the well-bearing component, the focus of the observation component is adjusted to focus on the wells.

In an embodiment of the present invention, the reference point is used to delineate a border of the image of the respective well in the image of the well-bearing component. In an embodiment of the present invention, the border delineated is substantially a circle about the reference point.

In an embodiment of the present invention, the reference point is the image of the focal point.

In an embodiment of the present invention, the reference point is the center of the image of the focal point.

In an embodiment of the present invention, c (acquiring an image of the focal point of a well-bottom) precedes d (acquiring at least one image of the well-bearing component).

In an embodiment of the present invention d (acquiring at least one image of the well-bearing component) precedes e (using the image of the focal point of the well-bottom to determine a reference point for identifying an image of a respective well in the image of the well-bearing component).

In an embodiment of the present invention, during step (d), a plurality of time-dependent images of the well-bearing components are acquired.

In an embodiment of the present invention, c (acquiring an image of a focal point (imaginary or real) of a well-bottom) is performed during d (acquiring at least one image of the well-bearing component). In an embodiment of the present invention, c is performed more than once during d.

In an embodiment of the presetn invention, the image of the well-bearing component is pixelated.

In an embodiment of the present invention, a group of pixels is designated as corresponding to the image of a respective well, based on the reference point. In an embodiment of the present invention, values related to the group of pixels are summed so as to yield a signal characteristic of the respective well. In an embodiment of the present invention, the values are related to an intensity of light acquired by the observation component from a part of the respective well. In an embodiment of the present invention, the values are related to an intensity of component frequencies of light acquired by the observation component from a part of the respective well.

In an embodiment of the present invention, at least one image of the well-bearing component is stored, preferably as digital data. In an embodiment of the present invention, prior to storing, the amount of digital data stored is reduced by removing and/or discarding data not corresponding to images of the wells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 (prior art) depicts a cell-chip device of PCT patent application IL01/00992 including a transparent carrier;

FIG. 2 (prior art) is a reproduction of a photograph of a cell-chip device of PCT patent application IL01/00992;

FIG. 3 (prior art) is a reproduction of a photograph of a cell-populated well-array of a carrier of a cell-chip device of PCT patent application IL01/00992;

FIG. 4 (prior art) is an image of MALT-4 cells on a glass plate where the borders of the cells are delineated by prior art image processing methods;

FIGS. 5A and 5B are flow charts of embodiments of the method of the present invention;

FIGS. 6A and 6B are schematic depictions of an embodiment of a device of the present invention useful in implementing the method of the present invention;

FIG. 7 is a reproduction of a scanning electron micrograph of an array of wells of a well-bearing component;

FIG. 8 is a reproduction of a scanning electron micrograph of a template used for producing an array of wells of a well-bearing component;

FIG. 9 is a depiction of the refractive properties of typical plano-concave well-bottoms;

FIGS. 10A-10E are depictions of an array of pixels visually representing an image as stored by an image processing component;

FIGS. 11A and 11B are reproductions of images of focal points of well-bottoms of a well-bearing component acquired in accordance with the teachings of the present invention;

Figure 11A:
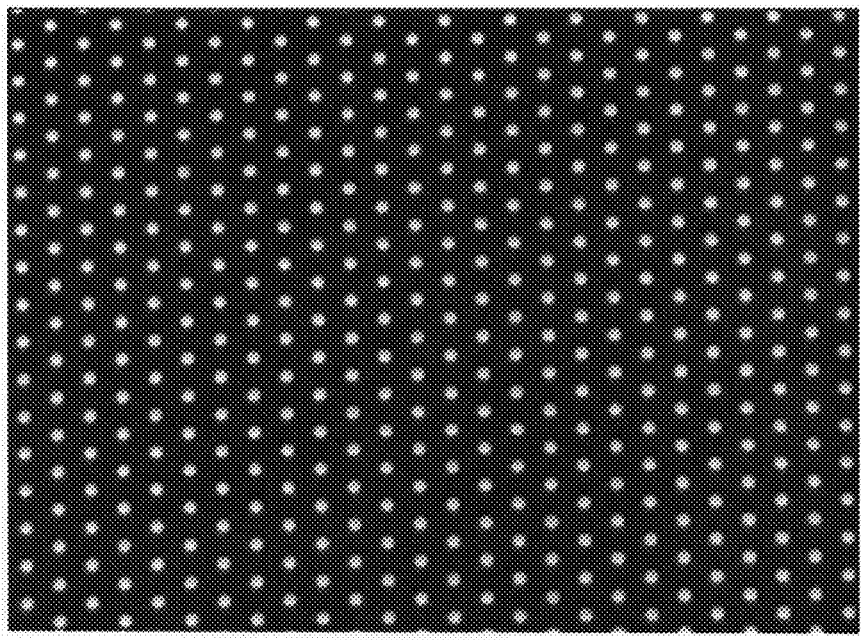
Figure 11B:
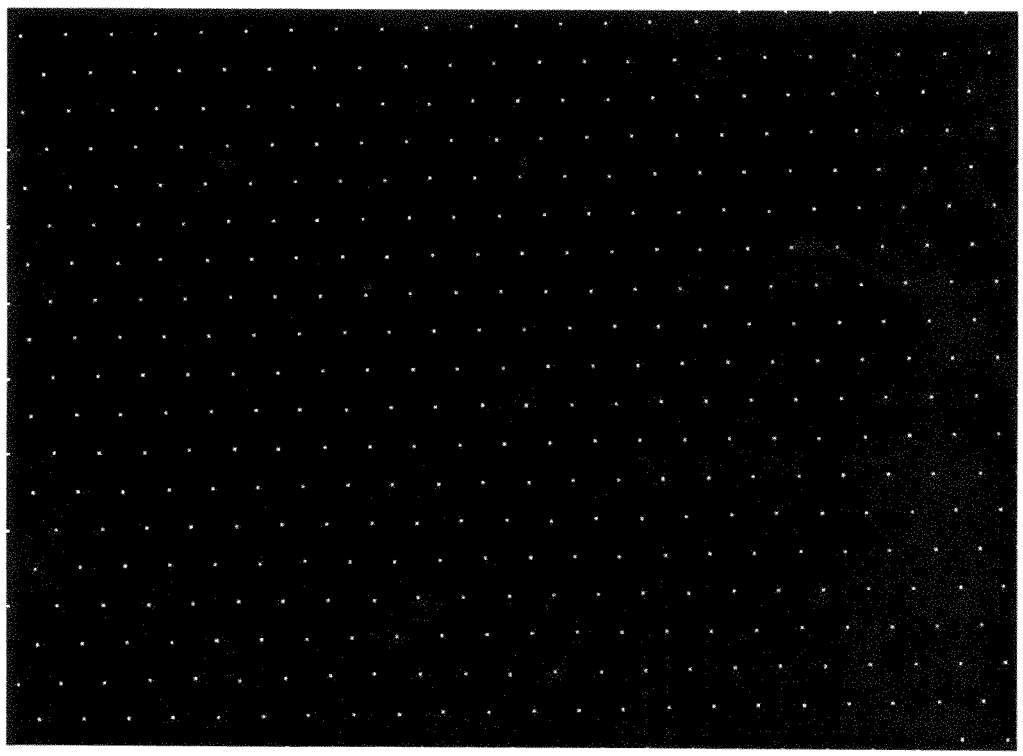
Figure 11C:
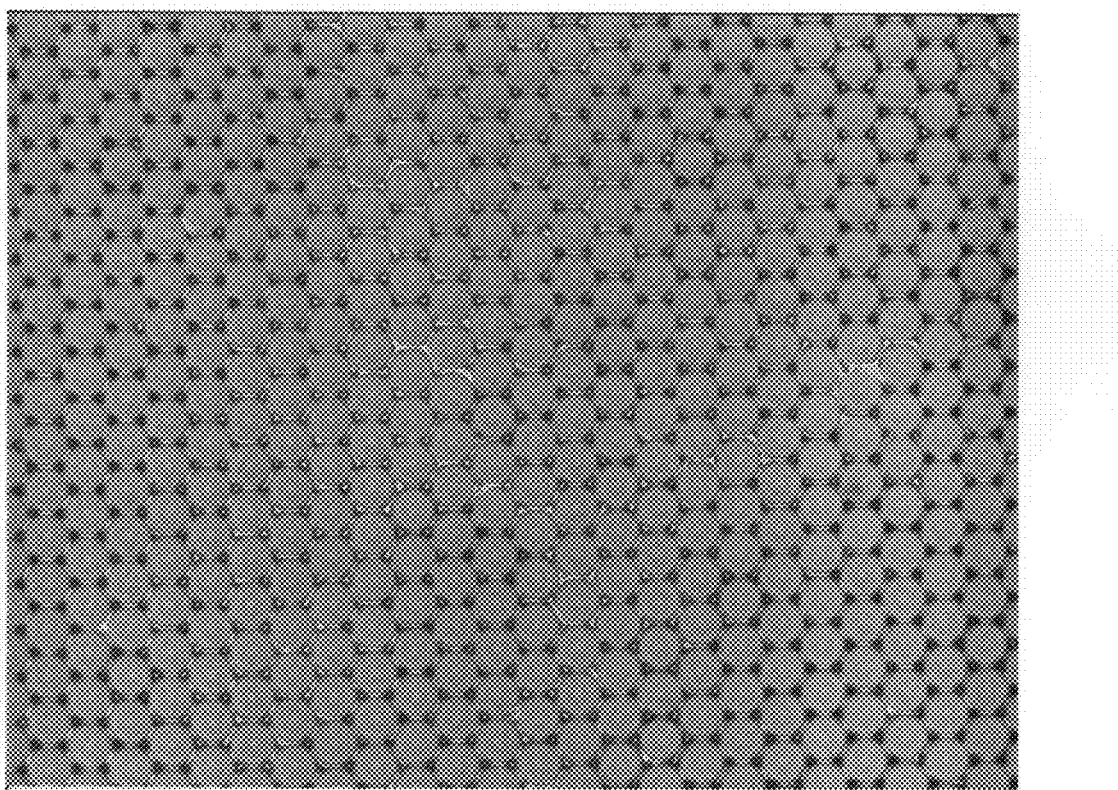
Figure 12:
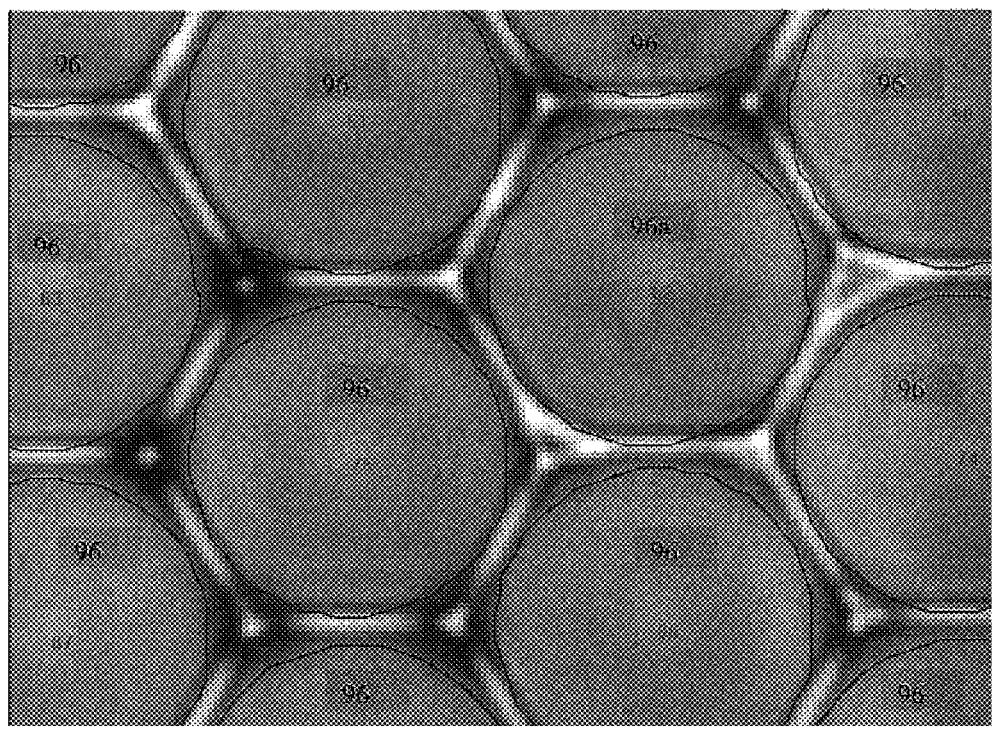
Figure 13A:
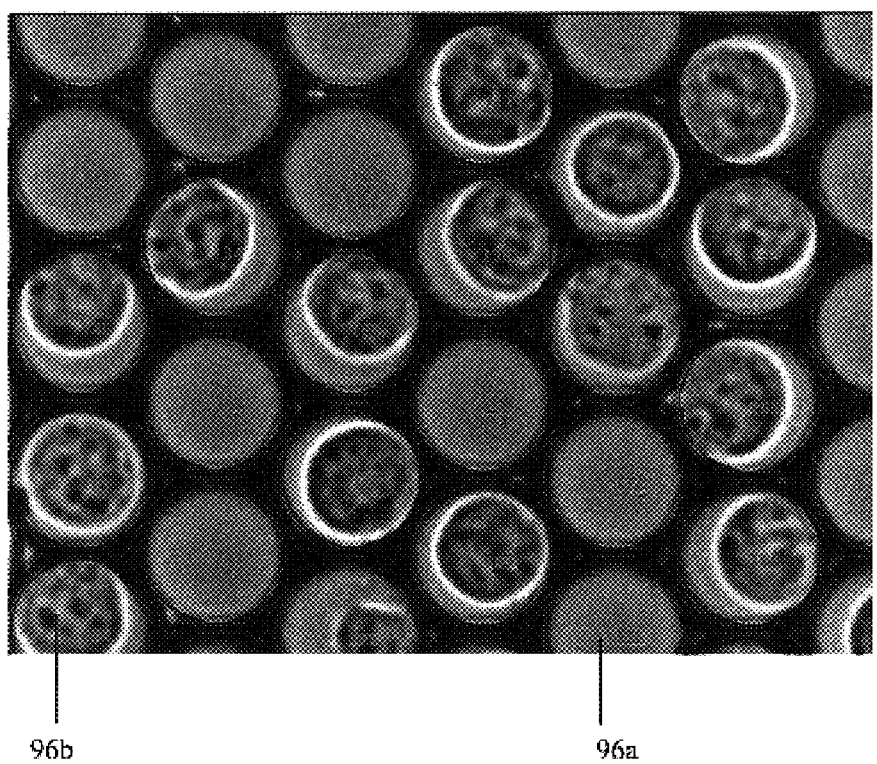
Figure 13B:
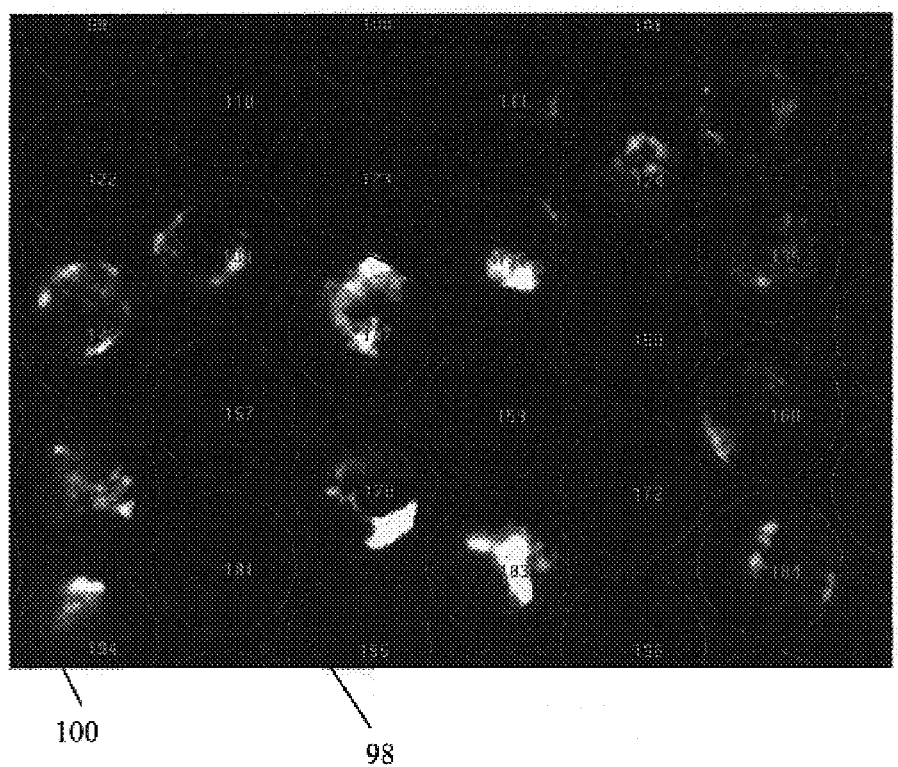
Figure 14A:
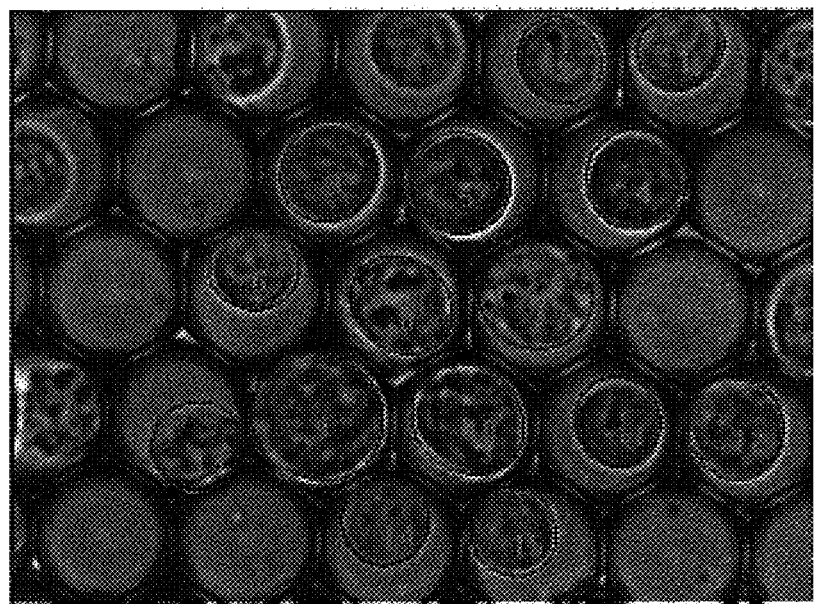
Figure 14B:
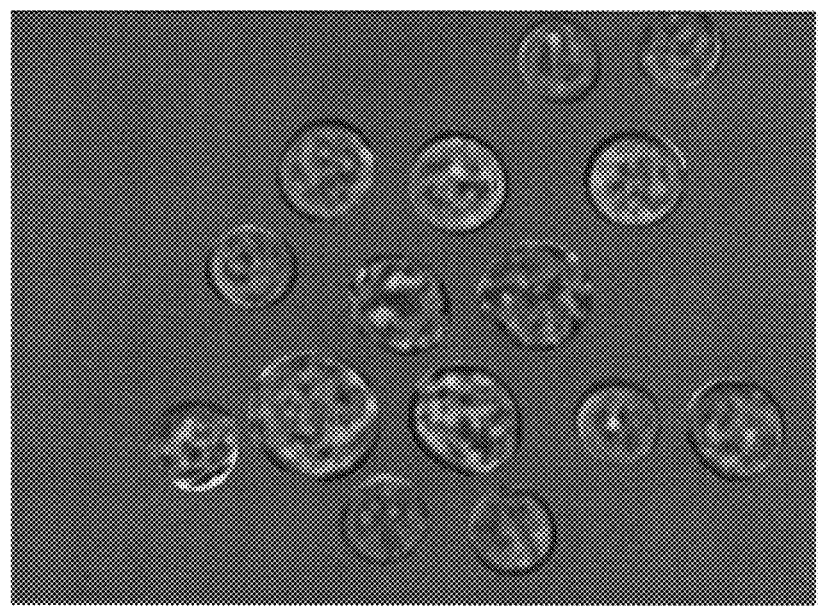
Figure 15A:
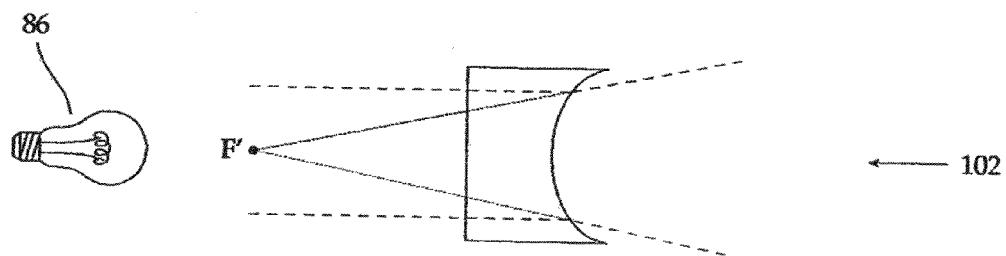
Figure 15B:
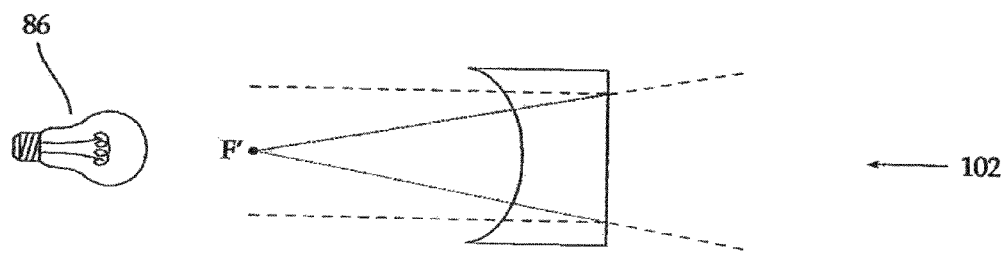
Figure 15C:
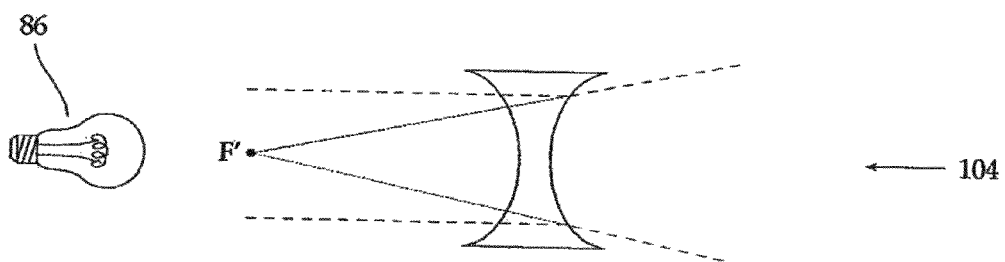
Figure 15D:
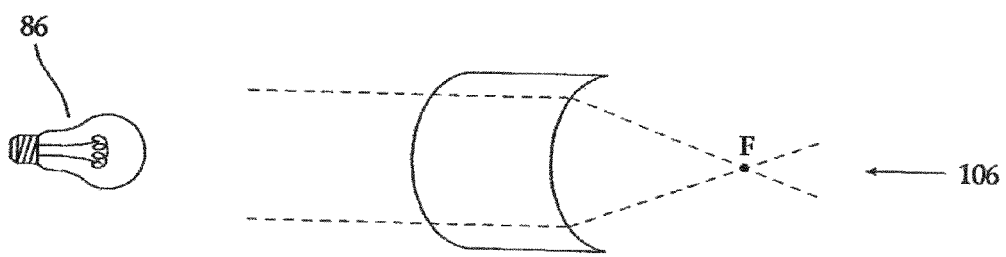
Figure 15E:
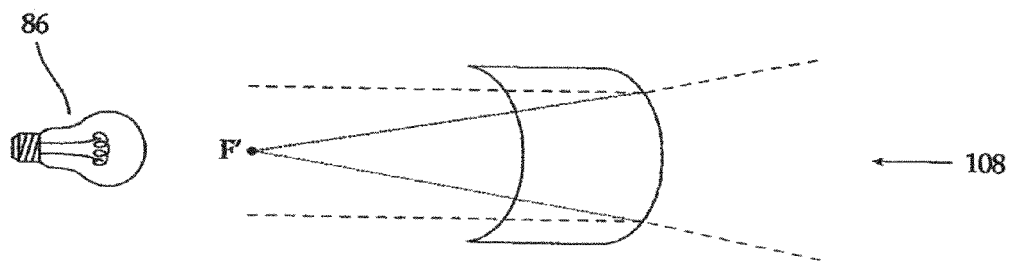
Figure 15F:
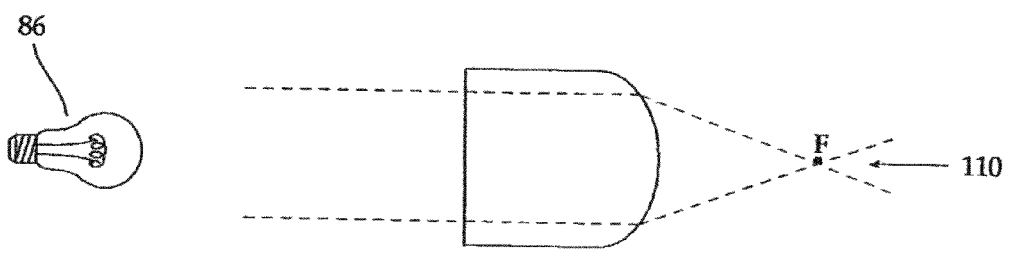
Figure 15G:
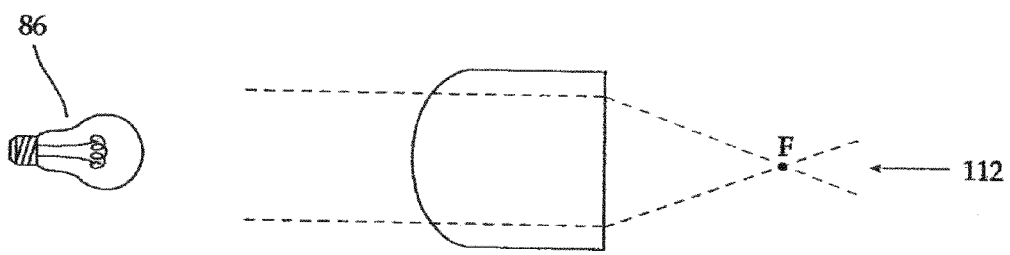
Figure 15H:
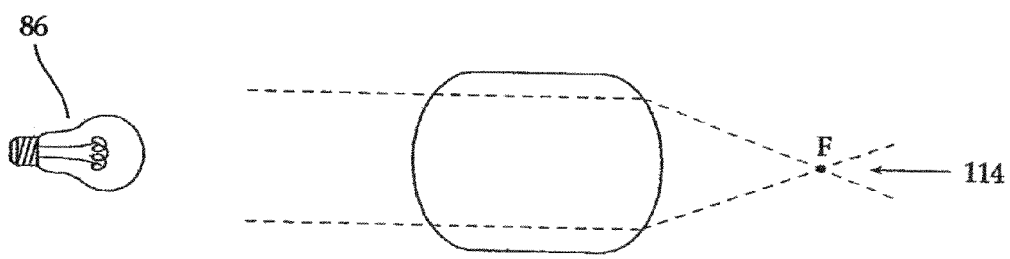
Figure 16:
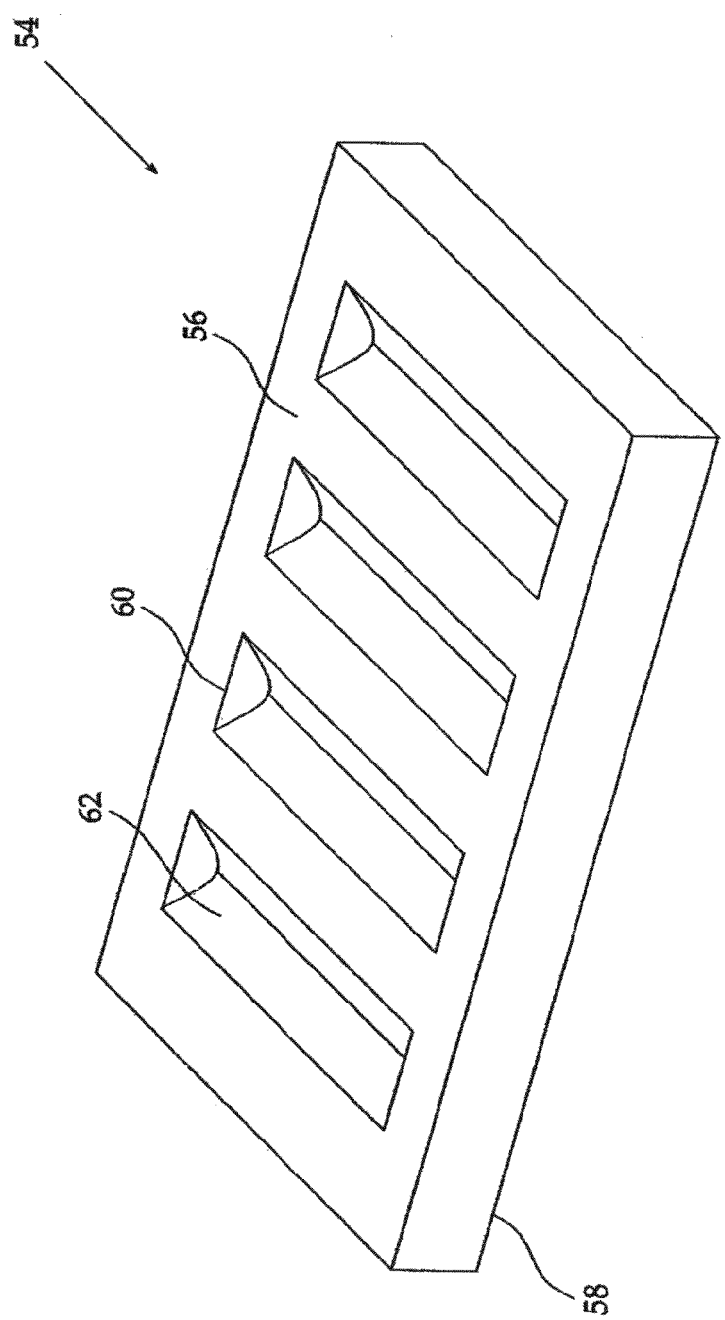
Figure 17:
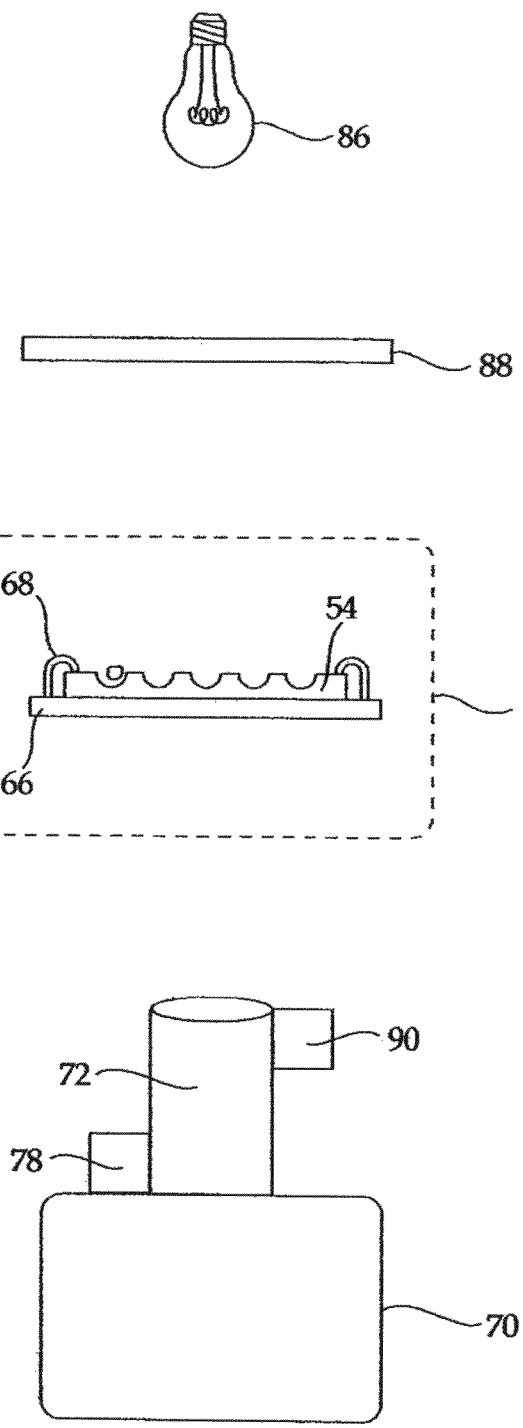

FIG. 11C is a reproductions of an image of a well-bearing component of FIGS. 11A and 11B acquired while focusing on the individual wells;

FIG. 12 is a reproduction of an image of a well-bearing component where images of individual wells are identified and delineated in accordance with the teachings of the present invention;

FIGS. 13A and 13B are reproductions of images of a well-bearing component holding MALT-4 cells, where images of individual wells are identified and delineated in accordance with the teachings of the present invention;

FIGS. 14A and 14B are reproductions of images of a well-bearing component holding MALT-4 cells, where images of cells held in individual wells are identified and delineated whereas images of inter-well areas are discarded in accordance with the teachings of the present invention;

FIG. 15 is a depiction of the refractive properties of typical well-bottoms;

FIG. 16 is a schematic depiction of a well-bearing component with wells having well bottoms with a $C_2$ rotation axis; and FIG. 17 is a schematic depiction of an embodiment of a device of the present invention useful in implementing the method of the present invention.

DESCRIPTION OF EMBODIMENTS OF THE INVENTION

The present invention is of a method for identifying an image of a well in an image of a well-bearing component, for example in the field of biology during optical study of cells. The present invention is also of a device useful in implementing the method of the present invention.

The principles, uses and implementations of the teachings of the present invention may be better understood with reference to the accompanying description and figures. Upon perusal of the description and figures present herein, one skilled in the art is able to implement the teachings of the present invention without undue effort or experimentation. In the figures, like reference numerals refer to like parts throughout.

Before explaining at least one embodiment of the invention in detail, it is to be understood that the invention is not limited in its application to the details set forth herein. The invention can be implemented with other embodiments and can be practiced or carried out in various ways. It is also understood that the phraseology and terminology employed herein is for descriptive purpose and should not be regarded as limiting.

Generally, the nomenclature used herein and the laboratory procedures utilized in the present invention include techniques from the fields of biology, chemistry and engineering. Such techniques are thoroughly explained in the literature. Unless otherwise defined, all technical and scientific terms used herein have the same meaning as commonly understood by one of ordinary skill in the art to which the invention belongs. In addition, the descriptions, materials, methods and examples are illustrative only and not intended to be limiting. Methods and materials similar or equivalent to those described herein can be used in the practice or testing of the present invention. All publications, patent applications, patents and other references mentioned are incorporated by reference in their entirety as if fully set forth herein. In case of conflict, the specification herein, including definitions, will control.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Implementation of the methods of the present invention involves performing or completing selected tasks or steps manually, automatically, or a combination thereof.

Herein, the term "active entity" is understood to include chemical, biological or pharmaceutical entities including any natural or synthetic chemical or biological substance that influences a cell with which the entity interacts. Typical active entities include but are not limited to active pharmaceutical ingredients, antibodies, antigens, biological materials, chemical materials, chromatogenic compounds, drugs, enzymes, fluorescent probes, immunogenes, indicators, ligands, nucleic acids, nutrients, peptides, physiological media, proteins, receptors, selective toxins and toxins.

Herein, by "indicator" is meant any active entity that upon interaction with some stimulus produces an observable effect. In the context of the present invention, by stimulus is meant, for example, a specific second active entity (such as a molecule) released by a cell and by observable effect is meant, for example, a visible effect, for example a change in color or emission of light, for example by fluoresence.

Herein, by "pixelation" is meant the process by which an image is divided into many small discrete elements (pixels), the pixels together constituting the image. By pixelation is also meant the process that occurs when an image is projected onto a pixelated detector, such as a CCD or CMOS detector array so that each part of the image is detected by a different discrete light-responsive element, so that the output of each light-responsive element is a pixel.

Embodiments of the present invention include components that are transparent or are made of a transparent material. By "transparent" is meant that the component or material is substantially transparent to radiation having a wavelength in at least part of the visible light spectrum, the ultraviolet light spectrum and/or of infrared radiation.

The method of the present invention is useful in the study of living cells. As is discussed in the introduction, it is known to study cells held, individually or in groups, in wells of a well-bearing component such as a multi-well plate or a cell-chip carrier (such as discussed in PCT patent application IL01/00992). In the art it is common to focus an observation component on the cells or the well and acquire images, whether non-time dependent images or signals (stills) or as a series of images so as to acquire time-dependent images or signals. Subsequently, the acquired images are pixelated and the borders of the individual wells delineated by image-analysis techniques. Existing image-analysis techniques require large amounts of resources and give insufficient results, often failing to differentiate between two wells.

The present invention is a method for identifying an image of a well in an image of a well-bearing component. Once an image of a well is identified, the present invention allows delineation of the borders of the image of the well. For pixelated images, the method of the present invention allows designation of specific pixels as being components of the image of a specific well. As is discussed hereinbelow in detail, such a designation of pixels allows for the use of an observation component, such as a CCD camera, as a high-speed multi-channel detector useful in high-throughput screening methods whilst retaining high-resolution optical data.

Implementation of the present invention is dependent on using an observation component to observe a well-bearing component where the bottoms of the wells have optical properties. The method of the present invention includes approaching focus of a real focal point or of an imaginary focal point of the well-bottom so as to acquire an image of light passing through the well-bottom that is preferably smaller than and preferably included within the image of the well when focusing on the well. The image of the well-bottom focal point is then used to determine a reference point to identify the image of the well in the image of the well-bearing component and from which to delineate the borders of the well.

In a preferred embodiment of the present invention, the bottom of the well has a $C_\infty$ rotation axis. Preferably, the $C_\infty$ rotation axis is substantially perpendicular to the focal plane of the observation component and the observation component is configured to acquire the image of the focal point substantially perpendicularly to the upper surface of the well-bearing component so that the image of the focal point is centered about the center of the image of the well. In a preferred embodiment, the observation component is focused on the real or imaginary focal point so that the image of the focal point is substantially a point of light substantially located in the center of the image of the well.

In a preferred embodiment, the borders of the well are delineated as defining a circle of a certain radius about the image of the focal point. In a preferred embodiment, the pixels found within the circle of the certain radius are designated as being components of the image of the well.

The method of the present invention allows for quick, accurate and robust delineation of the borders of a well. Some or all embodiments of the present invention have many advantages including:

identification of wells whether occupied or unoccupied by cells;

delineation of signal-less wells;

use of pixelating observation components (e.g., CCD or CMOS detectors) as multi-channel detectors;

delineation irrespective of well-bearing component orientation; and location of observation component above or below the well-bearing component.

The method of the present invention is a part of a process for gathering optical data for the study of cells held in well-bearing components. Although the method of the present invention is described herein for the study of cells held in a picowell-bearing microchip carrier such as discussed in PCT patent application IL01/00992 where each picowell holds one or other small number of cells, the teachings of the present invention are also applicable for the study of cells held in wells larger than picowells such as nanowells or microwells, as found in well-known and commercially available well-bearing components such as multiwell plates having 6, 12, 48, 96, 384 or 1536 wells.

It is assumed that the method of the present invention is implemented for studying a cell held in a well having a refractive transparent well-bottom, where there is a light source on one side of the well-bottom and an optical observation component having a variable focus on the other side of the well-bottom. By refractive transparent well-bottom is meant that light passing through the well-bottom is refracted.

Figure 1:
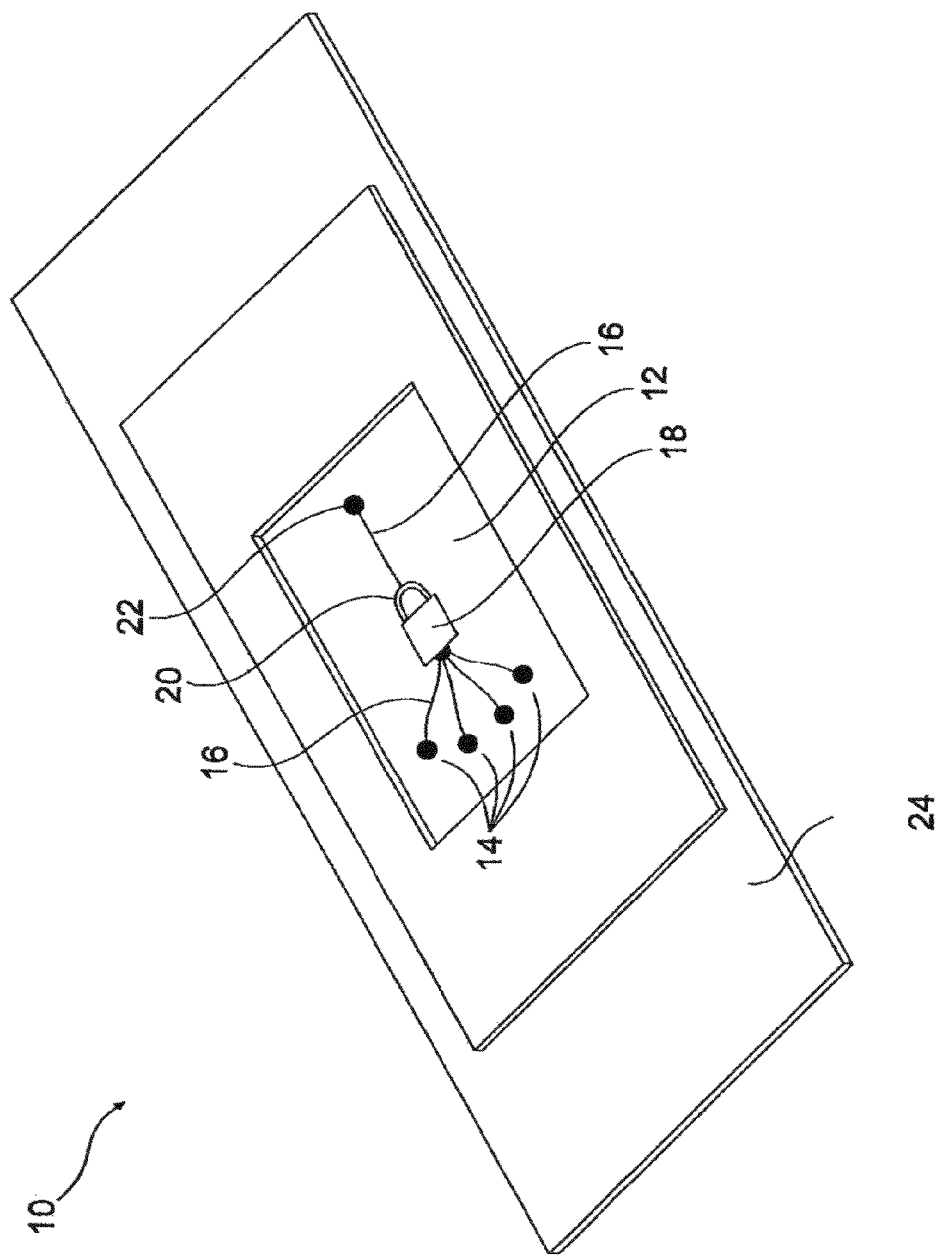
Figure 2:
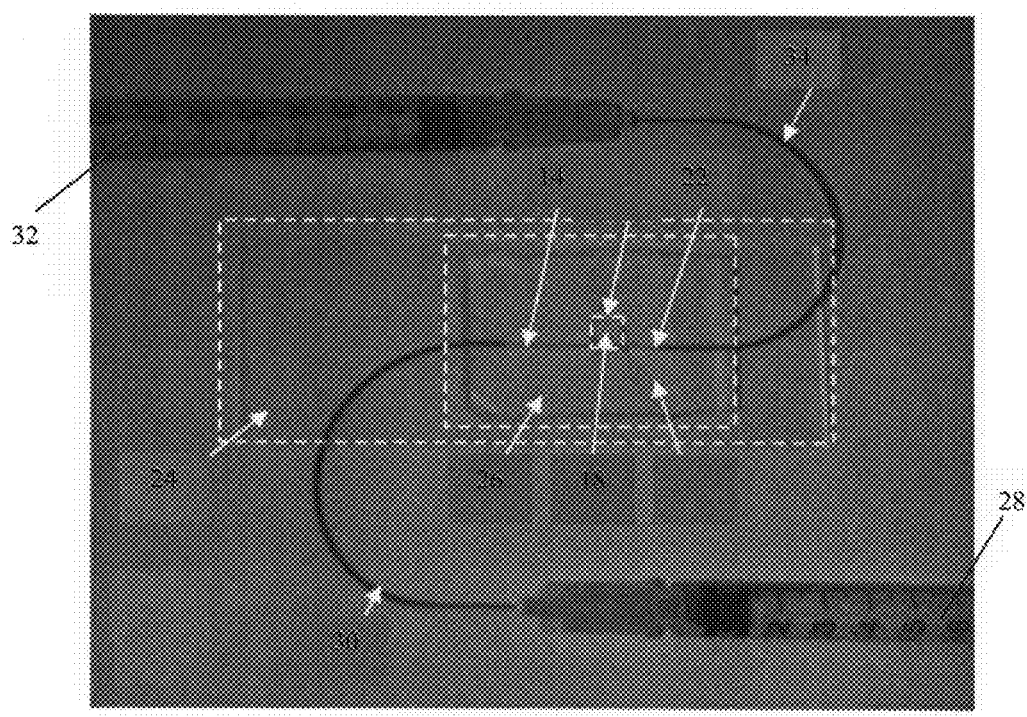
Figure 3:
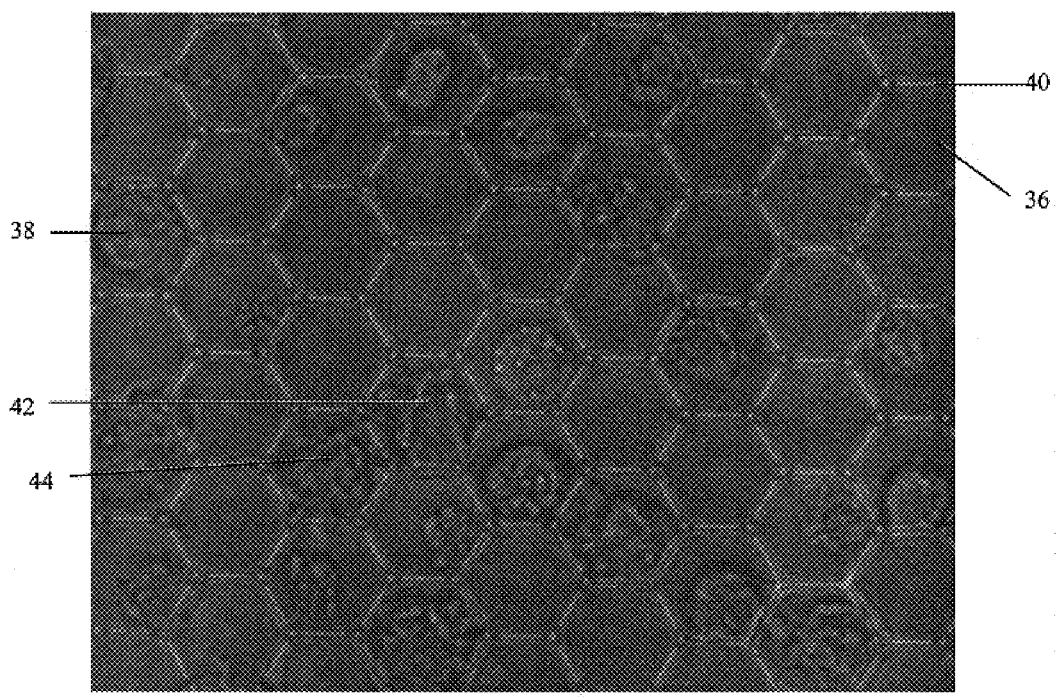
Figure 4:
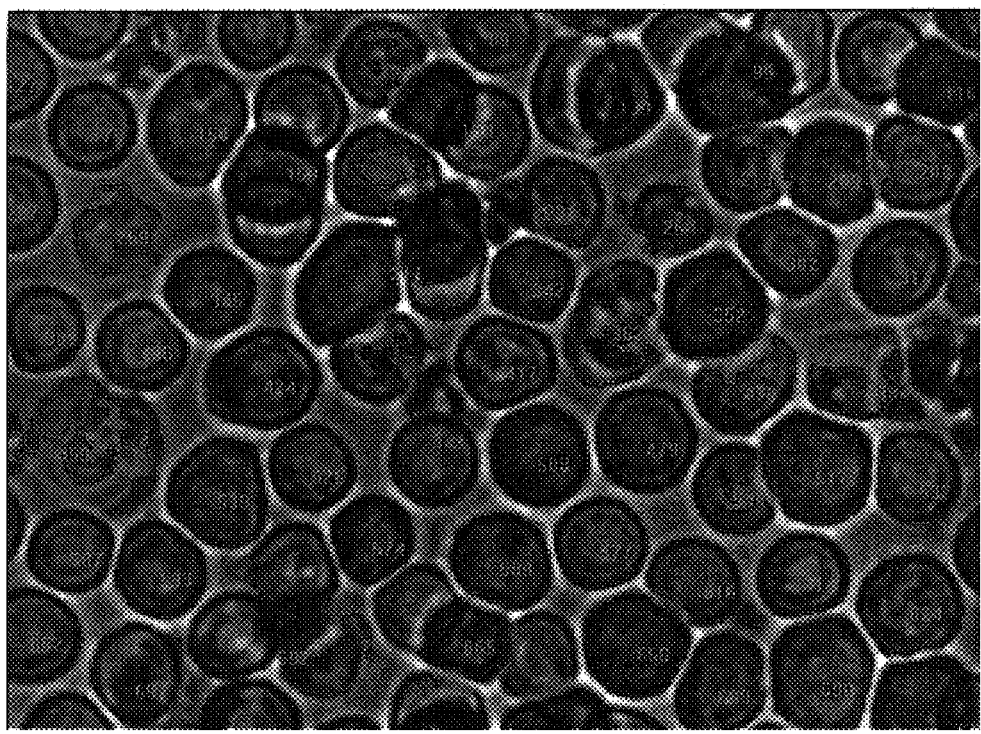
Figure 5A:
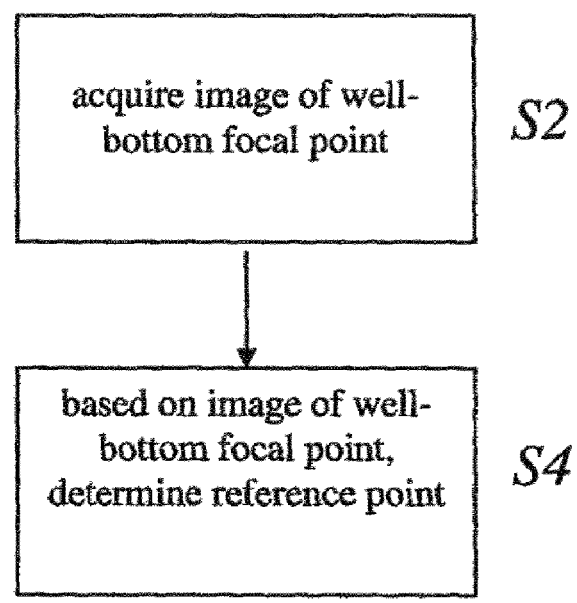
Figure 5B:
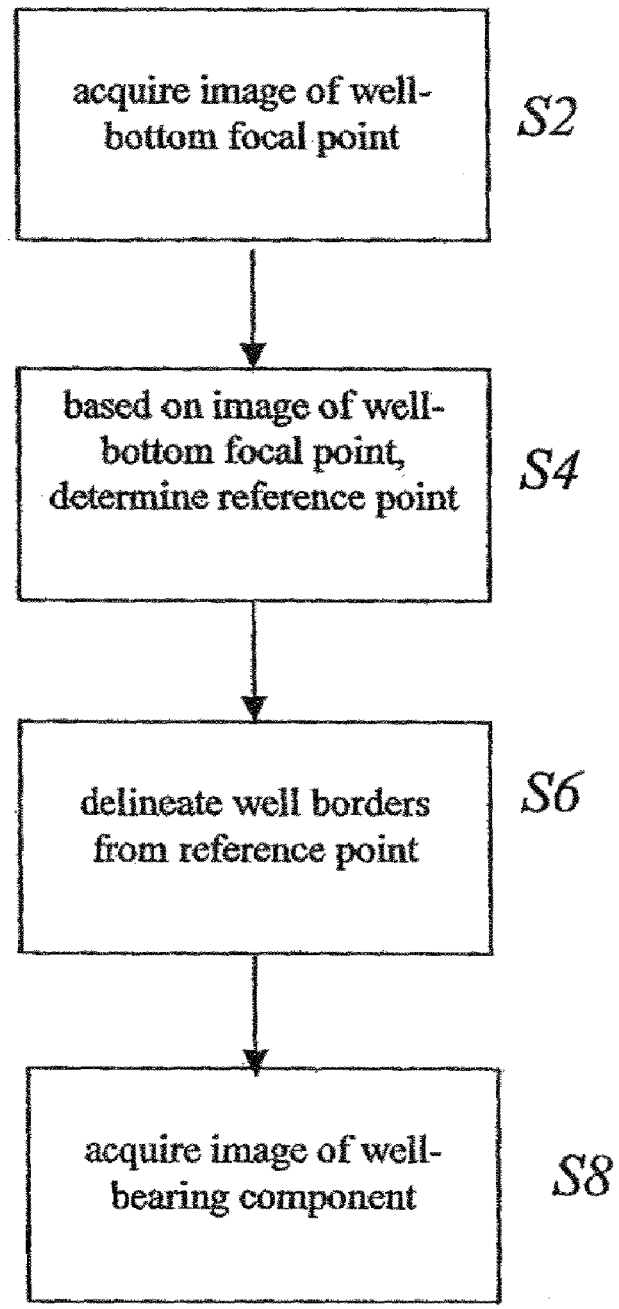

The embodiment of the present invention that is currently considered to be the best mode of implementing the method of the present invention is described by the flow charts depicted in FIGS. 5A and 5B. In FIG. 5A are depicted two steps, S2 and S4, of the method of the present invention. In FIG. 5B are depicted steps S2 and S4 together with two additional steps S6 and S8 making up the currently known best mode of implementing the teachings of the present invention for actually studying cells.

In step S2, the observation component is used to acquire an image of a real or imaginary focal point of the bottom of the well. In step S4, a reference point from which the the image of the well is identified is determined based on the image of the focal point. In step S6, the borders of the well are delineated by reference to the determined reference point. In step S8, optical data comprising an image of the well-bearing component is acquired. As is discussed hereinbelow, the optical data acquired in step S8 is of any type including high-resolution optical data or signal data.

As is discussed hereinbelow in greater detail, the order of performing the steps as depicted in FIG. 5B is not an important feature of the present invention. For example, depending on the embodiment, step S2 is performed before, during or after step S8. It is important to note, however, that in a preferred embodiment of the present invention, step S2 and step S8 are performed so that the images acquired in each step respectively are superimposable. This is most conveniently performed by using the same observation component to perform both step S2 and step S8 without changing the orientation of the well-bearing component relative to the observation component.

Figure 6A:
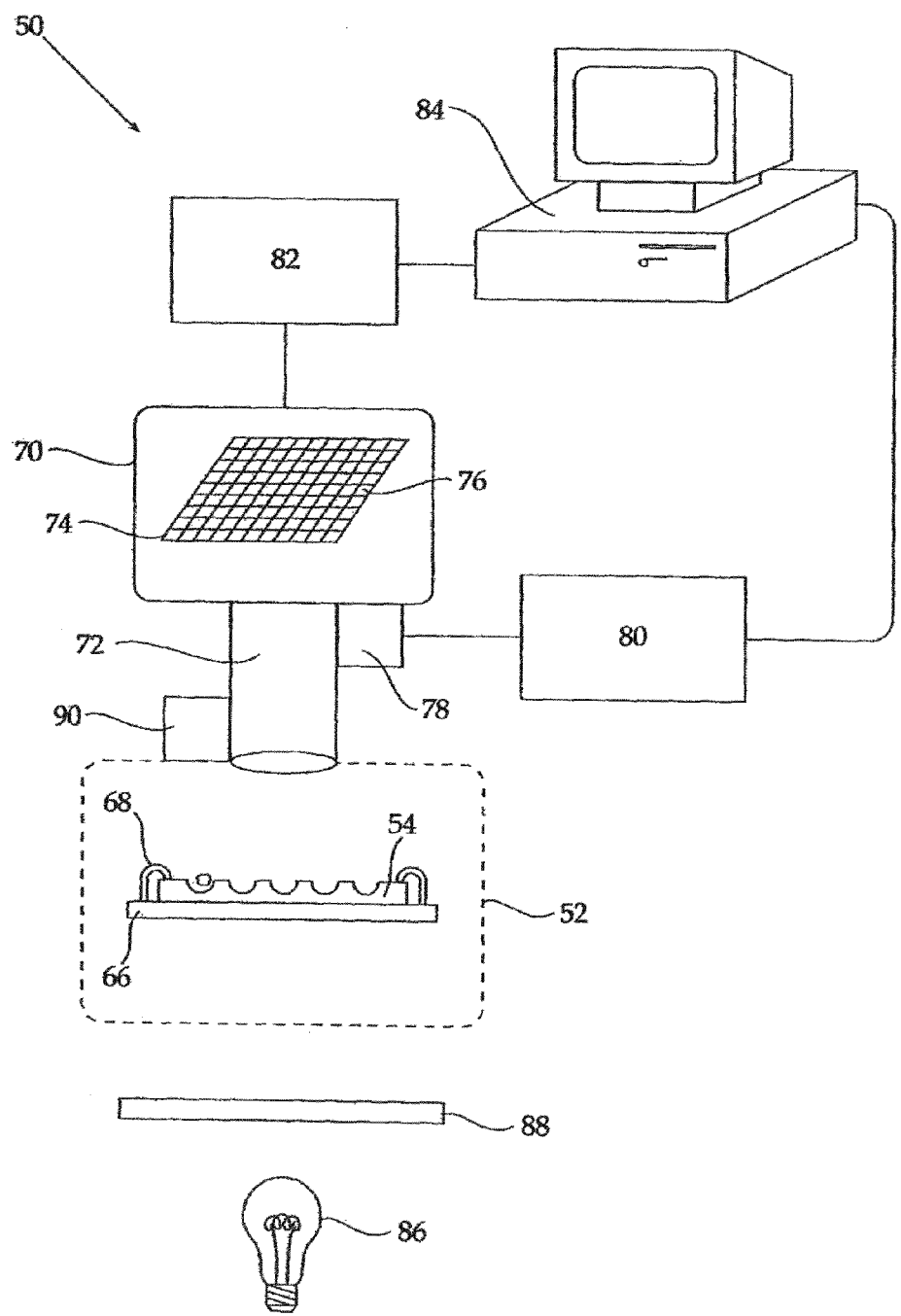
Figure 6B:
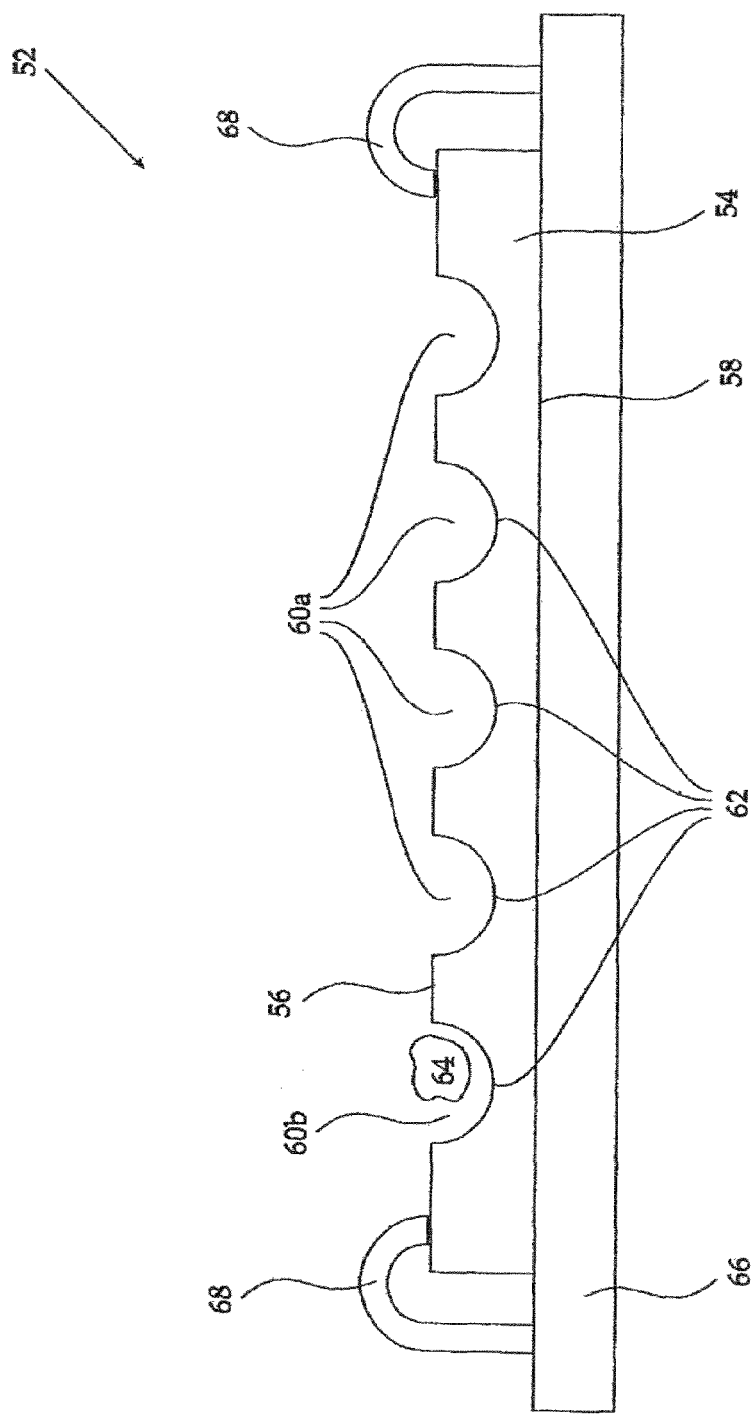

A preferred embodiment of the the method of the present invention is described in greater detail with reference to a device 50, schematically depicted in FIGS. 6A and 6B. In FIG. 6A, device 50 is schematically depicted. In FIG. 6B, an enlarged view of components found in box 52 are schematically depicted.

Device 50 includes a substantially planar glass well-bearing component 54 having an upper surface 56 and a substantially planar lower surface 58. On upper surface 56 is disposed a plurality of wells 60, wells 60 having a diameter of 20 micron and refractive transparent well-bottoms 62. Some wells 60b hold living cells 64 whereas some wells 60a do not hold living cells.

Figure 7:
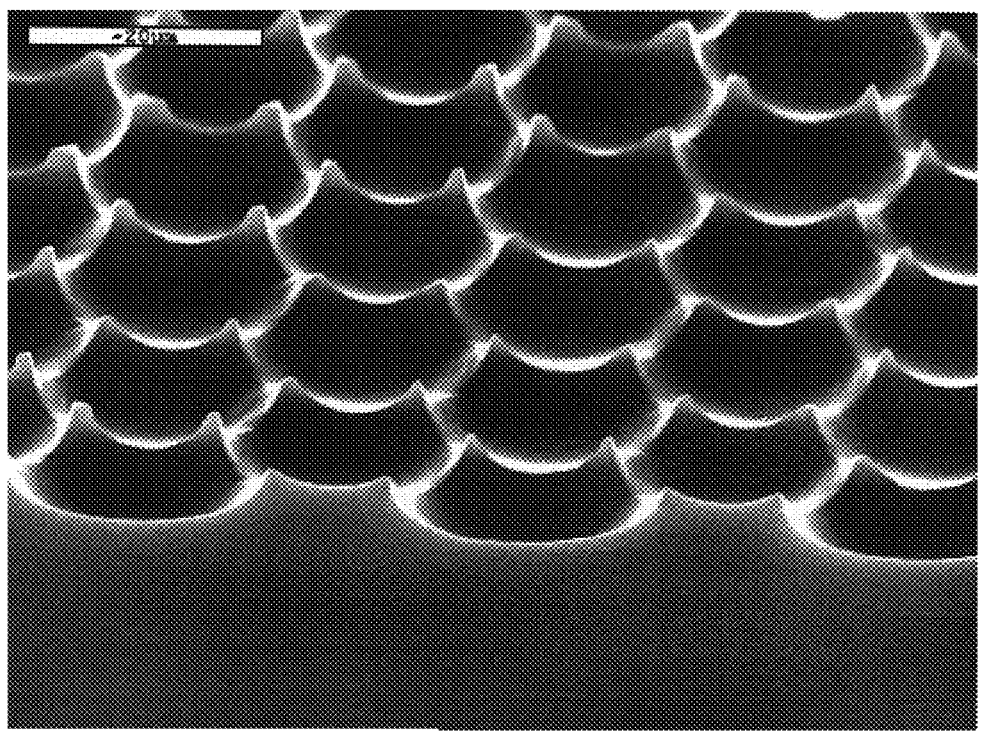
Figure 8:
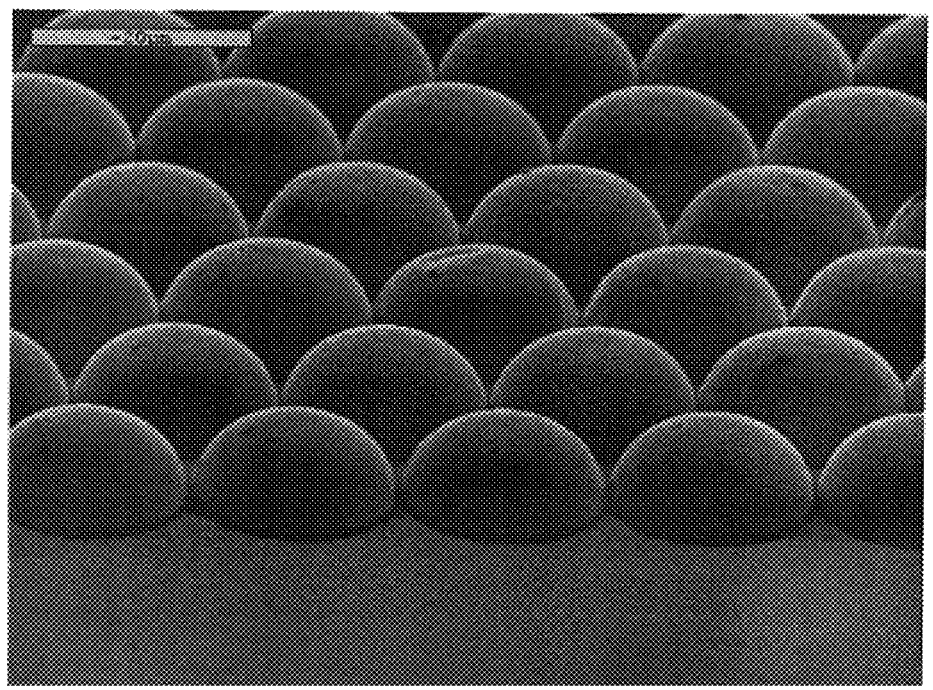

Well-bearing component 54 is substantially a carrier of a cell-chip device made in accordance with the teachings of PCT patent application IL01/00992. In FIG. 7, a scanning electron micrograph of wells of a well-bearing component 54 is reproduced. Well-bearing component 54 and wells 60 are produced by a process including solidifying molten glass in contact with a nickel template comprising negatives of wells 60 as described in PCT patent application IL01/00992. An electron micrograph of a nickel template used for producing well-bearing component 54 is reproduced in FIG. 8. Since the negatives of wells 60 in FIG. 8 are hemispheres and since lower surface 58 of well-bearing component 54 is planar, well-bottoms 62 are substantially plano concave lenses having a $C_\infty$ rotation axis.

In FIGS. 6A and 6B, well-bearing component 54 rests upon a transparent support plate 66 and is held firmly in place by holders 68.

Disposed above upper surface 56 of well-bearing component 54 is an observation component 70, in FIG. 6 an Olympus BX61 motorized research microscope (Olympus America Inc., Melville, N.Y., USA). Observation component 70 includes an adjustable focus lens 72 and a detection array 74 of a plurality of light responsive elements 76 (in FIG. 6 a CCD array of a DP70 digital camera (Olympus America Inc., Melville, N.Y., USA)) to convert light impinging on detection array 74 into electronic signals. Adjustable focus lens 72 is functionally associated with a focusing motor 78 controlled by a focus control component 80. The focal plane of observation component 70 is substantially perpendicular to the $C_\infty$ rotation axis of well-bottoms 62.

Observation component 70 is functionally associated with an image processing component 82, substantially a computer configured with hardware and software to manipulate electronic signals received from detection array 74 as an image as well as to process the individual pixels of the image as desired. Commercially available software suitable for image processing is, for example, Image Pro Plus (Media Cybernics Inc., Silver Spring, Md., USA).

A control computer 84 is functionally associated with both focus control component 80 and image processing component 82.

A locating light source 86 is disposed below lower surface 58 of well-bearing component 54, that is, the side opposite the side where observation component 70 is disposed. In device 50, locating light source 86 is a light-emitting diode. Locating light source 86 in FIG. 6A is functionally associated with a collimator 88, collimator 88 functioning so that light produced by locating light source 86 passes through well-bottoms 62 substantially parallel to the $C_\infty$ rotation axes of well-bottoms 62.

An observation light source 90 is disposed above upper surface 56 of well-bearing component 54, that is, the same side where observation component 70 is disposed. In device 50, observation light source 90 is a light-emitting diode.

Figure 9:
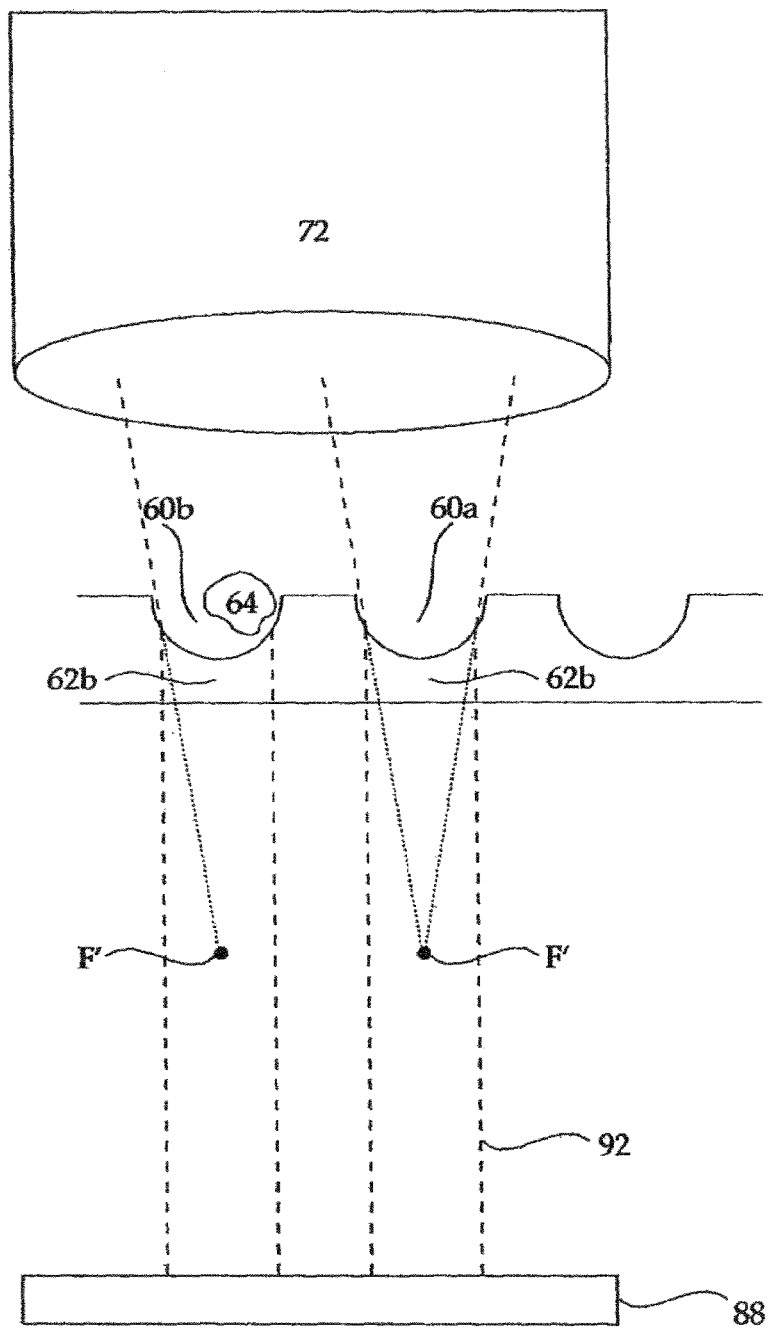

In FIG. 9, the refractive properties of a well-bottom 62a of a well 60a are depicted. As well-bottom 62a is substantially a symmetrical plano concave lens, light 90 from locating light source 86 passing collimator 88, through and emerging from well-bottom 62a diverges so as to form an imaginary focal point F'.

An embodiment of the method of the present invention implemented using a device 50, and with reference to FIGS. 5A, 5B, 6A, 6B, 9 and 10 is now discussed.

In step S2, an image of a real or imaginary focal point of the bottom of the well is acquired. Since, in FIGS. 5A, 5B, 6A, 6B and 9 well-bottoms 62 are divergent lenses, the focal points are imaginary focal points F'.

To acquire an image of the imaginary focal points, locating light source 86 is activated and light impinging on detection array 74, after passing through well-bottoms 62 and adjustable focus lens 72, is converted into an image by image processing component 82. The image is sent to control computer 84. Control computer 84 sends commands to focusing control component 80 to activate focusing motor 78 to adjust the focus of adjustable focus lens 72 while monitoring the changes in the image sent from image processing component 82 resulting therefrom.

Unlike prior art methods where an effort is made to adjust adjustable focus lens 72 to focus light from a cell 64 onto detection array 74 and thus acquire a high-resolution image of cell 64, according to the method of the present invention, adjustable focus lens 72 is adjusted to concentrate light 92 diverging from the imaginary focal point F' of well-bottom 62 of well 60 onto detection array 74.

In FIGS. 10A-10E, is depicted a 9 by 20 array 93 of 180 pixels 95 representing a visual representation of an image as stored by image processing component 82. In each one of FIGS. 10A-10E appear two circles 97 each delineating a group 99 of pixels. Each delineated group 99 of pixels is considered by image processing component 82 to define a respective circle 97.

Figure 10A:
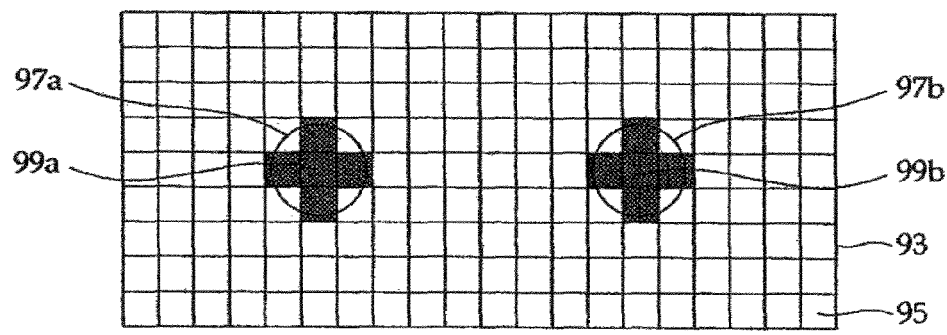

Images of the imaginary focal points of well-bottoms 62a and 62b as stored by image processing component 82 are depicted in FIG. 10A. It is seen that each image is represented by five activated pixels 95.

It is important to note that the method of the present invention is, unlike prior art methods, equally effective for identifying the images of occupied and empty wells. In FIG. 9 are depicted two wells, an empty well 60a and an occupied well 60b holding a cell 64. As discussed above for well 60a, light 92 from locating light source 86 passes through collimator 88, passes through well-bottoms 62a and 62b of wells 60a and 60b, respectively, and diverges. Light 92 is gathered by adjustable focus lens 72. Adjustable focus lens is set to concentrate light 92 from imaginary focal points F' onto detection array 74 forming images of the imaginary focal points. When comparing the images of the respective imaginary focal points F' formed by well-bottoms 62a and 62b, it is important to note that since adjustable focus lens 72 is used to concentrate light 92 diverging from a single imaginary focal point F' for each well-bottom 62a and 62b, cell 64 held in well 60b reduces the intensity of a respective image, but does not change the location of that image on detection array 74. For similar reasons, the location of a cell 64 held within a respective well 60b does not change the relative location of a respective image.

Figure 10B:
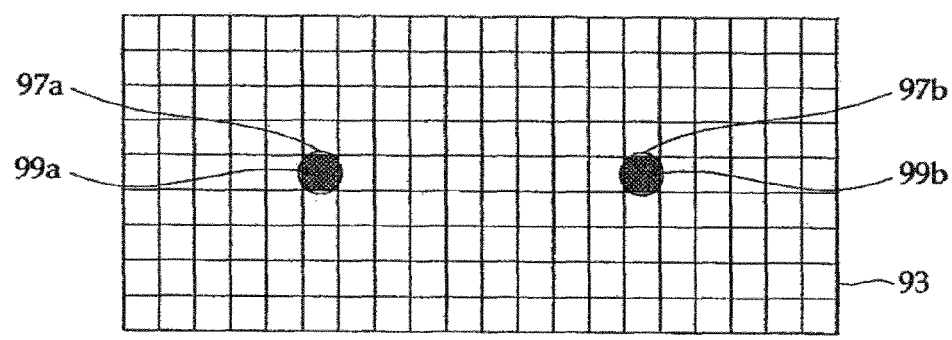

Since the presence of a cell 64 in a well 60b may significantly reduce the intensity of an acquired image of an imaginary focal point of a respective well-bottom 62b, in some embodiments of the present invention it is preferred to focus the light from a focal point of a well-bottom as much as possible so as to ensure that the light impinges on a small an areas as possible (for pixelated detectors, on as few light responsive elements of a respective detection array as possible). In such a way, even when a very large proportion of light passing through a given well-bottom is blocked by a cell held in the respective well, the image of the imaginary focal point of the well-bottom is easily acquired and identified. A schematic depiction of the images of the imaginary focal points of well-bottoms 62a and 62b after focusing all light from each well-bottom on a single light responsive element 76 as stored by image processing component 82 is depicted in FIG. 10B. It is seen that each image is represented by one pixel 95.

Although it is advantageous to focus all light from a well-bottom on a single. pixel, it is undesirable to spend much time focusing during the performance of step S2. Therefore in some embodiments of the present invention, during step S2, adjustable focus lens 72 is adjusted to a predetermined focus setting that is expected to produce sufficiently intense images of the focal points of the well bottoms. In an alternative embodiment, the setting of adjustable focus lens 72 is varied with continuous monitoring of the intensity of light impinging on light responsive elements 76 of detection array 74 by image processing component 82. When the maximum intensity of light impinging on light responsive elements 76 corresponding to the center of an image of an imaginary focal point of one, some or all well-bottoms 62 is passed, a desired degree of focus is considered to have been achieved.

Figure 10C:
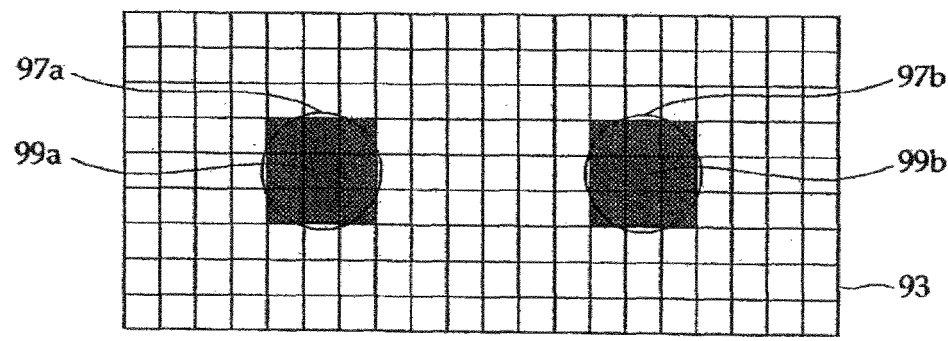
Figure 10D:
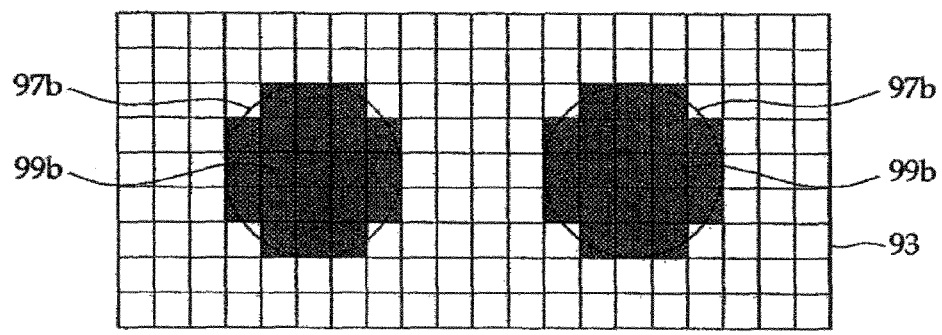

Once a desired degree of focus is achieved, a pattern of light spots 94 separated by darker areas is produced on detection array 74 by well-bearing component 54, as depicted in FIGS. 11A and 11B, light spots 94 being the images of the imaginary focal points of well-bottoms 62. In FIG. 11A is seen an image acquired after adjustable focus lens 72 is set to a predetermined setting, producing relatively large, diffuse light spots 94. In FIG. 11B is seen an image acquired after an effort is made to focus on the focal points, producing very sharp light spots 94. In FIG. 11C is seen an image acquired after adjustable focus lens is set to focus on wells 30. It is important to note that when FIGS. 10A, 10B and 10C are superimposed, sharp light spots 94 of FIG. 11B are found in the exact center of diffuse light spots 94 of FIG. 11A and in the exact center of wells 36 of FIG. 11C.

From light spots 94 corresponding to images of well-bottoms 62, a reference point for identifying the image of each respective well 60 is determined, step S4, followed by delineation of the borders of the images of the wells, step S6.

In a prefered embodiment of the present invention, both step S4 and step S6 are image processing steps performed by control computer 84, image processing component 82 or both. Although one skilled in the art recognizes that image processing is performed by manipulating an electronically stored digital representation of an image, the method of the present invention is described with reference to an image as the accepted and most understandable way of describing image processing processes. A device comprising hardware, software or a combination thereof for electronically storing a digital representation of an image and manipulating the image as required for implementing the method of the present invention is easily provided by one skilled in the art without undue effort or experimentation upon reading the description herein.

In an embodiment of step S4 of the present invention, a light spot 94 (or more accurately, the representation of an image of light spot 94, such as 99 in FIG. 10A or FIG. 10B) is designated to be a reference point for identifying an image of a respective well 60.

In an embodiment of step S4 of the present invention, a reference point for identifying an image of a well 60 is designated as a group 99 of one or more pixels constituting a respective light spot 94. In a preferred embodiment, the pixel or pixels constituting the center of group 99 are designated to be a reference point for identifying the image of a respective well 60. The identification of a pixel or pixels constituting the center of a group of pixels 99 is well-known to one skilled in the art.

Once a reference point for each image of each desired well 60 is designated, the borders of each image of each well 60 are delineated, step S6. It is important to note that what is meant by delineating the borders of an image of a well 60 is that the portion of an acquired image of a well-bearing component 54 that corresponds to the image of the well 60 is determined. When the image of a well-bearing component 54 is pixelated, what is meant is that the pixels that constitute the image of well 60 are determined.

It is a simple matter for one skilled in the art to delineate an area of an image or to designate pixels as belonging to a certain group of pixels in relationship to a reference point, once the reference point has been determined. Discussed herein in detail is a preferred embodiment of step S6 of the present invention, where the images of the focal points are pixelated and the reference point for any given well is the group of pixels 99 corresponding to light spot 94 (e.g., groups 99a and 99b in FIG. 10A) or the pixels at the center of group 99 (e.g., groups 99a and 99b in FIG. 10B).

In a first step, for each well 60, a respective reference point is designated to be the group of pixels 99 constituting a substantially circular, central part of a respective focal point image, e.g., groups 99a and 99b in FIG. 10A or 10B.

In a second step, for each well 60, the radius of the substantially circular group of pixels 99 that is a reference point is increased. The second step is repeated until any two substantially circular reference points of two neighboring wells are separated by a certain predetermined distance, for example one, two, three or more pixels.

Figure 10E:
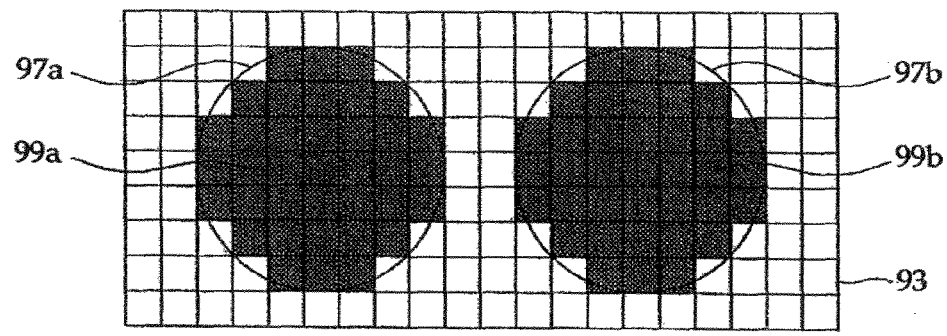

In an embodiment of the present invention, the second step of increasing the radii of the reference points is performed incrementally, for example by one pixel per cycle. Such an incremental process is graphically depicted by the changes from FIG. 10A (or FIG. 10B) to FIG. 10C, FIG. 10C to FIG. 10D and FIG. 10D to FIG. 10E. In FIG. 10E, group 99a and group 99b are separated by one pixel.

In another embodiment of the present invention, the second step of increasing the radii of the reference points is performed in one step by calculating the appropriate radii from the coordinates of the reference points. Such a process is graphically depicted by the changes from FIG. 10A (or FIG. 10B) to FIG. 10E.

Since, in a preferred embodiment, well-bottom 62 of a well 60 has a $C_\infty$ rotation axis perpendicular to the focal plane of observation component 70 the image of the imaginary focal point F' of well-bottom 62 is located in the center of an eventually formed image of well 60. In other words, if adjustable focus lens 72 is adjusted so as to focus on features of well 60 or of a cell 64 held in well 60, the light reflected from the center of well 60 impinges on the same light responsive elements 76 of detection array 74 as light 92 diverging from the imaginary focal point F'.

The result of step S4 is the establishment of a reference point from which to identify a part of an image of a well-bearing component 54 corresponding to an individual well 60. The result of step S6 is the delineation of an area of an image of well-bearing component 54 corresponding to an individual well 60. In embodiments of the present invention, the results of step S4 and S6 are used by image processing component 82 and control computer 84, for example, to identify the location of a well 60 and to focus onto that well 60. In preferred embodiments of the present invention, the results of step S4 and S6 are used by image processing component 82 and control computer 84 to analyze and output only selected data from all acquired data. The selected data analyzed or output is that corresponding to wells 60 or to specific wells 60 having certain characteristics.

Thus, subsequent to step S4 and S6, if it is desired to study only an image of a single well 60, image processing component 82 and control computer 84 analyze and display only areas corresponding to that single well 60. For a pixelated image only pixels corresponding to wells 60 are analyzed and displayed. For example, in FIG. 10E, pixels of an image of a well-bearing component 54 belonging to a group 99a are considered to make up an image of an individual cell and are analyzed and displayed as such.

Hereinbelow, step S8 will be described with reference to device 50 and as if step S8 is performed subsequently to step S2, step S4 and step S6. The description of the steps in such an order is considered to be the simplest to understand.

In step S8, the desired optical data is acquired as an image of well-bearing component 54, preferably using observation component 70. In an embodiment of the present invention, the optical data gathered is time-dependent. In an embodiment of the present invention, the optical data gathered is not time-dependent.

Generally, but not necessarily, locating light source 86 is deactivated. According to embodiments of the present invention, for example when it is desired to observe light reflected from cells 64 held in wells 60 or to acquire high-resolution optical data, observation light source 90 is activated. In other embodiments of the present invention, for example when the optical data gathered is light emitted by fluoresence of cells 64 or active ingredients such as indicators, observation light source 90 is not necessarily activated.

Generally, but not necessarily, adjustable focus lens 72 is set to focus on objects of interest held in wells 60 such as cells 64.

In an embodiment of the present invention, the optical data acquired is a high-resolution image of objects of interest, for example, images of cells 64 held in wells 64 of well-bearing component 54. Since the area of the high-resolution image acquired that corresponds to the image of each well 64 of interest is delineated according to the method of the present invention, automatized study of a specific individual well 60 or cell 64 with no overlap with neighboring objects and no identity confusion is simple. In an embodiment of the present invention, the data acquired by light responsive elements 76 of detection array 74 designated as corresponding to the image of a given well 60 are designated as being part of the image of the well 60 with no confusion or overlap with images of other wells 60.

Once the image of an individual well is delineated as described hereinabove, it is possible to use prior art image analysis methods to identify the borders of a cell held within a given individual well. Once the borders of a cell are determined it is a simple matter to estimate the volume or surface area of the cell. In some studies, it is informative to normalize detected signals relative to cell volume or cell surface area in order to make intercell comparisons.

In an embodiment of the present invention, data not designated as corresponding to images of wells 60 (for pixelated images, data not belonging to a group of pixels 99) is designated as corresponding to interwell area and is discarded as such data includes no useful information. In such a way, resources needed to store the data are reduced.

In an embodiment of the present invention, the optical data acquired is not a high-resolution image but rather signal data from objects of interest, for example light emitted by fluoresence of cells 64 or active entities held in wells 60 of well-bearing component 54.

In an embodiment of the present invention, exceptionally suitable for high-throughput screening methods, data corresponding to an acquired image of a single well is converted to a single signal. For example, the data from from all light responsive elements 76 of detection array 74 (or different colors summed separately, as may be appropriate) designated as corresponding to the image of a given well are summed. In such a way, observation component 70 is used as a multichannel detector, each channel being the intensity of light (or the intensity of light of a certain color) detected as having been emitted from a specific well.

In an embodiment, optical data acquired is a high-resolution image of well-bearing component 54 as described above. The data (preferably excluding data corresponding to inter-well areas) is stored. Either subsequently or simultaneously, data acquired and designated as corresponding to each individual well 60 is summed so as to produce a single signal representative of the intensity of light impinging on detection array 74 from each individual well 60. When desired, all such signals are analyzed for certain characteristics (e.g., intensity or time-dependent behavior). The high-resolution images corresponding to wells 60 associated with signals having the certain characteristics are recovered and studied. In a preferred embodiment, the acquired high-resolution image of well-bearing component 54 is parsed into a plurality of high-resolution subimages, each subimage including only data corresponding to an image of a single well 60. Each such subimage is associated with a respective derived signal and independently stored for quick recovery. Such optical data storage is useful, for example, when it is desired to confirm that a given noteworthy signal intensity (high or low) is produced by a whole cell, a cell fragment or an empty well. Such optical data storage also allows differentiation between empty wells identified as having little or no detected signal and filled wells holding cells that produce little or no detected signal.

Hereinabove, the method of the present invention has been disclosed where step S2 is followed by step S4, step S4 is followed by step S6 and step S6 is followed by step S8, an order chosen exclusively for convenience of description. As is clear to one skilled in the art, performance of step S8 is not dependent on performance of any of steps S2, S4 or S6 and can be performed at any time before, after or during performance of steps S2, S4 or S6.

In a preferred embodiment of the present invention, the order of steps is as discussed hereinabove S2 followed by S4 followed by S6 followed by S8.

Since steps S4 and S6 are calculational steps dependent only on data acquired in step S2, steps S4 and S6 are performed whenever convenient. For example, in embodiments of the present invention such as the embodiment described hereinabove, steps S4 and S6 are performed immediately after step S2 and prior to step S8. In other embodiments of the present invention, steps S4 and S6 are performed after both step S2 and step S8 have been performed. For example, in embodiments where step S2 and step S8 include recording acquired images using a video camera as part of observation component 70, it is often convenient to digitize the acquired video data and subsequently perform steps S4 and S6 remotely from observation component (i.e., off-line) after steps S2 and S8 are completed.

Whether data acquired in step S8 is time-dependent or not time-dependent (e.g., stills) in embodiments of the present invention S2 precedes S8 whereas in other embodiments of the present invention S8 precedes S2.

In a preferred embodiment of the present invention, multiple steps S2 and S8 are performed alternately. Such a preferred embodiment is exceptionally useful when step S8 includes the acquisition of time-dependent data and is even more exceptionally useful when during step S8 there is motion of well-bearing component 54 in the X-Y plane, for example, due to intermittent scanning of well-bearing component 54.

Reproductions of images produced according to the method of the present invention are depicted in FIG. 12, FIGS. 13A and 13B and FIGS. 14A and 14B.

In FIG. 12 is depicted an image of a well-bearing component 54 devoid of cells 64 subsequent to steps S2, S4, S6 and S8. In FIG. 12, grey areas 96 delineated by a black, substantially circular, line is composed of pixels displaying data from a high-resolution image of a well-bearing component 54 designated as corresponding to an individual well 60. For example, area 96a is an image made up of data acquired only from a well designated 62. Between any two grey areas 96 is sumperimposed a simulated image of walls of wells 60 for the convenience of the viewer.

In FIGS. 13A and 13B are depicted two separate images of the same well-bearing component 54 holding MALT-4 cells.

In FIG. 13A is depicted a high-resolution image of a -well-bearing component 54 subsequent to step S2, step S4, step S6 and step S8. In some wells, 60 of well-bearing component 54 are held cells 64. As in FIG. 12, an area 96 delineated by black, substantially circular, lines is composed of pixels displaying high-resolution image data acquired from a well-bearing component 54 designated as corresponding to an individual well 60. It is seen that an image 96a of an empty well 60a is grey whereas an image 96b of a well 60b holding a cell 64 includes a high-resolution image of a respective cell 64. Between any two areas 96 is sumperimposed a simulated image of walls of wells 60 for the convenience of the viewer.

In FIG. 13B is depicted a high-resolution image of fluoresence detected coming from a well-bearing component 54 subsequent to a step S2, step S4, step S6 and step S8. In FIG. 13B, areas delineated by white, substantially circular, lines are composed of pixels displaying data acquired from a well-bearing component 54 designated as corresponding to an individual well 60. It is seen that images of empty wells or images of wells holding non-fluorescent cells, such as 98, are black whereas in images of wells holding fluorescent cells, such as 100, a fluorescent signal is apparent.

In FIGS. 14A and 14B are depicted two separate images of the same well-bearing component 54 holding MALT-4 cells.

In FIG. 14A is depicted a high-resolution image of a well-bearing component 54 subsequent to step S2, step S4, step S6 and step S8 and a further cell delineation step. In some wells, 60 of well-bearing component 54 are held cells 64. Subsequent to delineation of wells 60 as described hereinabove, image analysis was performed of each delineated well individually. As the borders of each well are delineated, it is a relatively simple matter to identify the borders of each cell against the background of the medium wherein the cells are found by an image analysis search only in the image of the well.

Thus, in FIG. 14A, it is seen that cells 60 of interest are delineated by a black line. Subsequently, all data not corresponding to cells 60 of interest is deleted, saving data storage resources. When desired, all cells 60 of interest are displayed in a single uncluttered image, FIG. 14B.

Hereinabove and in the Figures, the method of the present invention has been discussed where well-bottoms 62 are all substantially plano concave lens with a focal plane substantially parallel to the focal plane of observation component 70. Such a well-bottom shape is preferred for many reasons, including: a well-bearing component 54 having a planar lower surface 58 is simple to produce and easy to use; concave well-bottoms are easy to accurately produce (see PCT patent application IL01/00992); and a concave well-bottom is a natural shape for a well 60 configured to hold a cell 64. That said, the teachings of the present invention are applicable to substantially any shape of well-bottom.

As noted hereinabove and discussed hereinbelow, it is preferred that a well-bottom 62 have a $C_\infty$ rotation axis substantially perpendicular to to the focal plane of observation component 70. In FIG. 15 are depicted some, but not all, suitable well-bottom shapes in cross section, all having a $C_\infty$ rotation axis substantially perpendicular to to the focal plane of observation component 70. In FIG. 15, plano concave well-bottoms 102, bi concave well-bottom 104 and negative meniscus well-bottom 108 are substantially divergent lenses having an imaginary focal point F'. When the method of the present invention is implemented using well-bottoms that are substantially divergent lenses, adjustable focus lens 72 is used to focus on imaginary focal point F'. In FIG. 15, positive meniscus lens 106, plano convex lenses 110 and 112 and biconvex lens 114 are substantially convergent lenses having a real focal point F. When the method of the present invention is implemented using well-bottoms that are substantially convergent lenses, adjustable focus lens 72 is used to focus on real focal point F.

In some embodiments of the present invention, well-bottoms 62 have a $C_\infty$ rotation axis that is not substantially perpendicular to the focal plane of observation component 70. In other embodiments, well-bottoms 62 do not have a $C_\infty$ rotation axis. The disadvantages of well-bottoms 62 not having a $C_\infty$ rotation axis perpendicular to the focal plane of the observation component are discussed hereinbelow.

Hereinabove and in the Figures, the method of the present invention has been discussed where each well-bottom 62 has a rotation axis perpendicular to the focal plane of observation component 70. One advantage of a well-bottom rotation axis perpendicular to the focal plane of observation component 70 is that a single observation component 70 is easily used to identify the center of an image of a well 60 as a reference point for delineating the borders of the well-image by acquiring an image of a real or imaginary focal point of the respective well-bottom 62. The fact that the rotation axis is perpendicular to the the focal plane of observation component 70 means that for observation component 70 the image of the focal point is in the center of the image of the respective well 60. That said, in embodiments of the present invention, a well-bottom 62 does not have a rotation axis perpendicular to the focal plane of observation component 70. In such embodiments, the step of delineating the borders of an image of a well based on the image of a focal point of a respective well-bottom generally requires determination of an offset value.

Hereinabove and in the Figures, the method of the present invention has been discussed where each well-bottom 62 has a $C_\infty$ rotation axis. One advantage of a lens having a $C_\infty$ rotation axis is that the image of a focal point of such a lens is a point or a circle. As is clear to one skilled in the art, a point is a preferred shape for a reference point from which to delineate a circular or substantially circular well 62. As is clear to one skilled in the art and as described hereinabove, a circle-shaped image is easily converted to be a point or used as a reference point from which to delineate a circular or substantially circular well 62. An additional advantage of $C_\infty$ rotation axis is that any obstruction of light, for example, by the presence of a cell 64 held in a respective well 60b does not change the shape or location of the focal point image, as depicted in FIG. 9. That said, in embodiments of the present invention, well-bottoms 62 do not have a $C_\infty$ rotation axis and consequently the image of a focal point is not necessarily a point or a circle. Examples include well-bottoms 62 having a $C_2$ rotation axis, a $C_3$ rotation axis or a $C_4$ rotation axis. Such well-bottoms are exceptionally useful, for example, when the shape of a respective well 60 is substantially not circular, e.g., rectangular, triangular or square (see PCT patent application IL01/00992). Such well-bottoms are also exceptionally useful, for example, when there is significance to well orientation, for example when data is gathered for experiments performed under the influence of a magnetic field or during the flow of active compounds.

In an embodiment of the present invention, depicted in FIG. 16, well-bearing component 54 has a substantially planar lower surface 58 and an upper surface 56 on which a plurality of rectangular wells 60 are disposed with "hull-shaped" well-bottoms 62 in FIG. 16 having a $C_2$ rotation axis. As is clear to one skilled in the art, well-bottoms 62 are substantially divergent lenses producing an imaginary focal line. An image of such an imaginary focal line defines the long and short side of the image of each well 60, as well as the orientation of the respective well 60. Implementation of the method of the present invention for wells, such as depicted in FIG. 16, having a $C_2$ rotation axis including the retention of directional information is well within the ability of one skilled in the art upon perusal of the description and figures herein.

Hereinabove and in the Figures, the method of the present invention has been discussed where wells 60 are picowells and well-bearing component 54 is a carrier of a cell-chip device of PCT patent application IL01/00992. It is clear to one skilled in the art that the teachings of the present invention are applicable, with the appropriate modifications, to many different types of well-bearing components 54, including but not limited to well-bearing components such as multiwell plates having the well-known 6-well, 12-well, 48-well, 96-well, 384-well or 1536-well format, the well-bearing components described in unpublished copending PCT patent application IL04/00571 of the Applicant filed Jun. 27, 2004, and the well-bearing components described in unpublished copending PCT patent application IL04/00661 of the Applicant filed Jul. 20, 2004.

Hereinabove and in the Figures, the method of the present invention has been discussed where well-bottoms 62 are made of glass. Clearly a well-bottom 62 made of any material is suitable for implementing the teachings of the present invention as long as there exists at least one wavelength of light emitted by a locating light source 86 detectable by observation component 70, to which well-bottom 62 is substantially transparent and which is diffracted during passage through well-bottom 62. Suitable materials from which well-bottoms 62 of the present invention are made include materials mentioned in described in PCT patent application IL01/00992, in unpublished copending PCT patent application IL04/00571 of the Applicant filed Jun. 27, 2004 or in unpublished copending PCT patent application IL04/00661 of the Applicant filed Jul. 20, 2004. Such materials include but are not limited to gels, hydrogels, waxes, hydrocarbon waxes, crystalline waxes, paraffins, ceramics, elastomers, epoxies, glasses, glass-ceramics, plastics, polycarbonates, polydimethylsiloxane, polyethylenterephtalate glycol, polymers, polymethyl methacrylate, polystyrene, polyurethane, polyvinyl chloride, rubber, silicon, silicon oxide and silicon rubber.

Hereinabove and in the Figures, the method of the present invention has been discussed where locating light source 86 is below well-bearing component 54 and observation component 70 is above well-bearing component 54. Whereas in some embodiments of the present invention such a configuration is preferred, in other embodiments of the present invention it is preferred that locating light source 86 is above well-bearing component 54 and observation component 70 is below well-bearing component 54, as depicted in FIG. 17. As is understood from FIG. 15, such variation in configuration does not substantially influence the practice of the teachings of the present invention.

Hereinabove and in the Figures, the method of the present invention has been discussed where light produced by a locating light source 86 and passing through well-bottoms 62 is collimated by collimator 88. In a preferred embodiment of the present invention, images of focal points of well-bottoms 62 are acquired from substantially parallel light rays impinging on well-bottoms 62 in parallel to a rotation axis of well-bottoms 62. That said, embodiments of the present invention use non-collimated light, non-parallel light, or light that does not necessarily impinge in parallel to a rotation axis of a well-bottom 62. For example, in embodiments of the present invention it has been found that a diffuse locating light source 86 (e.g., a standard microscope condenser) placed sufficiently far away from lower surface 58 of a well-bearing component 54 yields images of focal points of respective well-bottoms 62 that are sufficiently defined for implementing the teachings of the present invention.

The method of the present invention is manually implementable. That said, it is clear to one skilled in the art that it is preferable that many steps be performed automatically. As is known to one skilled in the art, the simplest and most convenient way for implementing an automatic embodiment of the method of the present invention includes providing a computer device, such as control computer 84, together with appropriate hardware and software. All necessary hardware for implementing the teachings of the present invention is commercially available. Further, all software necessary for implementing the teachings of the present invention is commercially available or can be prepared by one skilled in the art without undue effort or experimentation upon perusal of the description and figures herein.

Hereinabove and in the Figures, the method of the present invention has been discussed where observation component 70 includes a digital camera equipped with a CCD sensor. Whereas in some embodiments of the present invention such an observation component is preferred (because CCD digital cameras pixelate images, because suitable CCD digital cameras are common and because CCD digital cameras are easily coupled to image processing components), in other embodiments of the present invention other types of obervation components are used. Suitable observation components include but are not limited to digital cameras equipped with CMOS sensors, film cameras and video cameras. It is important to note that in embodiments where the image acquired by observation component 70 is not pixelated but where steps S4 and step S6 are digital processes, it is usually necessary to include a pixelation step. In some embodiments of the present invention, the desired data is continuously pixelated for image processing, as described above. In other embodiments, the desired data is recorded and only subsequently pixelated for image processing.

Generally, the nomenclature used herein and the laboratory procedures utilized in the present invention include techniques from the fields of biology, chemistry and engineering. Such techniques are thoroughly explained in the literature.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, the present invention is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method for acquiring data comprising:
   a) providing a substantially planar well-bearing component having a lower surface, an upper surface, and a plurality of wells having refractive well-bottoms disposed on said upper surface and an observation component configured to observe a first of said two surfaces;
   b) projecting light through said well-bottoms from a second of said two surfaces;
   c) acquiring an image of a focal point of a said well-bottom using said observation component;
   d) acquiring at least one image of said well-bearing component using said observation component; and
   e) using said image of said focal point of said well-bottom to determine a reference point for identifying an image of a respective well in said image of said well-bearing component.

2. The method of claim 1, wherein said well-bottoms have a $C_\infty$ rotation axis.

3. The method of claim 2, wherein said $C_\infty$ rotation axis is substantially perpendicular to a focal plane of said observation component.

4. The method of claim 2, wherein said light is substantially parallel to said rotation axis.

5. The method of claim 1, wherein said first of said two surfaces is said lower surface and said second of said two surface is said upper surface.

6. The method of claim 1, wherein said first of said two surfaces is said upper surface and said second of said two surface is said lower surface.

7. The method of claim 1, wherein said light is collimated.

8. The method of claim 1, wherein said focal point is an imaginary focal point.

9. The method of claim 1, wherein said focal point is a real focal point.

10. The method of claim 1, further comprising prior to c, adjusting the focus of said observation component.

11. The method of claim 10, wherein said adjusting the focus of said observation component is to an extent where two images of two focal points produced by two well-bottoms are distinct.

12. The method of claim 11, wherein said adjusting the focus of said observation component is to an extent where the size of said image of said focal point is substantially minimal.

13. The method of claim 1, wherein said acquiring at least one image of said well-bearing component includes detecting light emitted by fluoresence.

14. The method of claim 1, wherein said acquiring at least one image of said well-bearing component includes detecting light reflected from said first of said two surfaces.

15. The method of claim 1, further comprising, prior to d, adjusting the focus of said observation component to focus on contents of said wells disposed on said upper surface of said well-bearing component.

16. The method of claim 1, further comprising, prior to d, adjusting the focus of said observation component to focus on said wells disposed on said upper surface of said well-bearing component.

17. The method of claim 1, further comprising using said reference point for delineating a border of said image of said respective well in said image of said well-bearing component.

18. The method of claim 17, wherein said border delineated is substantially a circle about said reference point.

19. The method of claim 1, wherein said reference point is said image of said focal point.

20. The method of claim 1, wherein said reference point is the center of said image of said focal point.

21. The method of claim 1, wherein c precedes d.

22. The method of claim 1, wherein d precedes e.

23. The method of claim 1, wherein during d, a plurality of time-dependent images of said well-bearing components are acquired.

24. The method of claim 23, wherein c is performed during d.

25. The method of claim 24 wherein c is performed more than once during d.

26. The method of claim 1, further comprising, pixelating said image of said well-bearing component.

27. The method of claim 26, further comprising, based on said reference point designating a group of pixels as corresponding to said image of a respective said well.

28. The method of claim 26, further comprising, summing values related to said group of pixels so as to yield a signal characteristic of said respective said well.

29. The method of claim 28, wherein said values are related to an intensity of light acquired by said observation component from a part of said respective said well.

30. The method of claim 28, wherein said values are related to an intensity of component frequencies of light acquired by said observation component from a part of said respective said well.

31. The method of claim 1, further comprising storing said at least one image of said well-bearing component.

32. The method of claim 31, wherein said at least one image is stored as digital data.

33. The method of claim 32, further comprising, prior to said storing, reducing the amount of said digital data stored by removing data not corresponding to images of said wells.

* * * * *